US012648939B2

(12) United States Patent
Gopinathan et al.

(10) Patent No.: US 12,648,939 B2
(45) Date of Patent: Jun. 9, 2026

(54) COMPOUNDS AND METHODS FOR TREATING SPASTICITY

(71) Applicant: Lexicon Pharmaceuticals, Inc., The Woodlands, TX (US)

(72) Inventors: Suma Gopinathan, The Woodlands, TX (US); Praveen Tyle, Spring, TX (US); Qi Melissa Yang, The Woodlands, TX (US)

(73) Assignee: LEXICON PHARMACEUTICALS, INC., The Woodlands, TX (US)

( * ) Notice: Subject to any disclaimer, the term of this patent is extended or adjusted under 35 U.S.C. 154(b) by 473 days.

(21) Appl. No.: 18/133,926

(22) Filed: Apr. 12, 2023

(65) Prior Publication Data

US 2023/0330074 A1 Oct. 19, 2023

Related U.S. Application Data

(60) Provisional application No. 63/331,547, filed on Apr. 15, 2022.

(51) Int. Cl.

| | |
|---|---|
| ***A61K 31/444*** | (2006.01) |
| ***A61P 21/00*** | (2006.01) |
| ***A61P 21/02*** | (2006.01) |
| ***A61P 25/14*** | (2006.01) |

(52) U.S. Cl.

CPC ............ *A61K 31/444* (2013.01); *A61P 21/00* (2018.01); *A61P 21/02* (2018.01); *A61P 25/14* (2018.01)

(58) Field of Classification Search

CPC ........ A61K 31/444; A61P 21/02; A61P 21/00; A61P 25/14

See application file for complete search history.

(56) References Cited

U.S. PATENT DOCUMENTS

| | | | |
|---|---|---|---|
| 9,902,722 | B2 | 2/2018 | Luo et al. |
| 10,155,760 | B2 | 12/2018 | Luo et al. |
| 10,246,469 | B2 | 4/2019 | Bronson et al. |

OTHER PUBLICATIONS

Kostich et al., The Journal of Pharmacology and Experimental Therapeutics, 358:371-386, Sep. 2016. (Year: 2016).*

Luo, et al., "Discovery of (S)-1-((2' ,6-Bis(difluoromethyl)-[2,4' -bipyridin]-5-yl)oxy)-2,4-dimethylpentan-2-amine (BMS-986176/ LX-9211): A Highly Selective, CNS Penetrable, and Orally Active Adaptor Protein-2 Associated Kinase 1 Inhibitor in Clinical Trials for the Treat", J Med Chem 65, 4457-4480 (2022).

Ashton, J , "Emerging treatment options for spasticity in multiple sclerosis—clinical utility of cannabinoids", Degener Neurol Neuromuscul Dis 1, 15-23 (2011).

Bundrant, L. , "Results of two Phase 1, Randomized, Double-blind, Placebo-controlled, Studies (Ascending Single-dose and Multiple-dose Studies) to Determine the Safety, Tolerab 1hty, and Pharmacokinetics of Orally Administered LX9211 in Healthy Participants", Clinical Therapeutics 43(6), 1029-1050 (2021).

Chang, E , et al., "A Review of Spasticity Treatments: Pharmacological and Interventional Approaches", Crit Rev Phys Rehabil Med 25 (1-2), 11-22 (2013).

Chou, R , et al., "Comparative efficacy and safety of skeletal muscle relaxants for spasticity and musculoskeletal conditions: a systematic review", J Pain Symptom Manage 28, 140-175 (2004).

Johnson, Michael , et al., "Reflex wind-up in early chronic spinal injury: plasticity of motor outputs", J Neurophysiol 117, 2065-2074 (2017).

Kishka, U , "Neurological rehabilitation and management of spasticity", Medicine 36, 616-619 (2008).

Lapeyre, E , et al., "Spasticity: revisiting the role and the individual value of several pharmacological treatments", Neuro Rehabilitation 27, 193-200 (2010).

Patent Cooperation Treaty , International Search Report and Written Opinion for PCT/US2023/018372, 12 pages dated Jul. 27, 2023.

Rabchevsky, A , et al., "Latest approaches for the treatment of spasticity and autonomic dysreflexia in chronic spinal cord injury", Neurotherapeutics 8, 274-282 (2011).

Stevenson, V , et al., "Neurological rehabilitation and the management of spasticity", Medicine 40, 513-517 (2012).

Adams, et al., "Spasticity after spinal cord injury", Spinal Cord 43, 577-586 (2005).

Li, et al., "Windup leads to characteristics of central sensitization", Pain 79, 75-92 (1999).

Mehta, et al., "A randomized trial of memantine as treatment for spasticity in multiple sclerosis", Multiple Sclerosis 16 (2), 248-251 (2010).

Price, et al., "The N-methyl-D-aspartate receptor antagonist dextromethorphan selectiveliy reduces temporal summation of second pain in man", Pain 59, 165-174 (1994).

Russo, et al., "Short-term plasticity in turtle dorsal horn neurons mediated by L-Type Ca2+ channels", Neuroscience 61 (2), 191-197 (1994).

Smith, et al., "Enhanced Bulbar Function in Amyotrophic Lateral Sclerosis: The Nuedexta Treatment Trial", Neurotherapeutics 14, 762-772 (2017).

Zhou, et al., "Targeting N-methyl-D-aspartate receptors for treatment of neuropathic pain", Expert Rev Clin Pharmacol 4 (3), 379-388 (2011).

* cited by examiner

*Primary Examiner* — Laura L Stockton

(74) *Attorney, Agent, or Firm* — Viksnins Harris Padys Malen LLP

(57) ABSTRACT

Provided herein are methods of treating and preventing spasticity in a patient in need thereof. A particular method comprises administering an effective amount of an adaptor associated kinase 1 inhibitor of Formula (I):

(I)

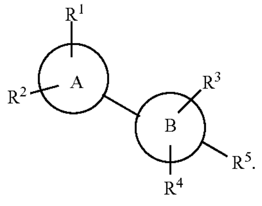

10 Claims, 9 Drawing Sheets

COMPOUNDS AND METHODS FOR TREATING SPASTICITY

CROSS-REFERENCE TO RELATED APPLICATIONS

This application claims priority to U.S. Provisional Application No. 63/331,547 filed Apr. 15, 2022, the entire contents of which are incorporated herein by reference.

FIELD OF THE INVENTION

This invention relates compounds, compositions, and methods useful in the treatment and prevention of spasticity.

BACKGROUND OF THE INVENTION

This invention relates compounds, compositions, and methods useful in the treatment and prevention of spasticity.

Spasticity is defined as a velocity-dependent increase in tonic stretch reflexes with exaggerated movements due to the hyperexcitability of stretch reflexes. Chang, E., et al., Crit Rev Phys Rehabil Med., 2013, 25(1-2): 11-22. It is a well-known phenomenon seen in patients of all ages with a wide range of central neurological disorders, and can be a feature of a single traumatic insult or from chronic neurological conditions. Id.; Stevenson V, Playford D., Medicine, 2012, 40:513-7. It is often recognized as one component of upper motor neuron syndrome, the motor control changes that are seen after damage to an upper motor neuron controlling voluntary skeletal movement. Some examples of upper motor neuron pathology include spinal cord injury (SCI), cerebral palsy, stroke, amyotrophic lateral sclerosis, and multiple sclerosis (MS). In fact, spasticity is the most commonly reported symptom for MS, seen in 90% of patients with the disorder. Ashton J C., Degener Neurol Neuromuscul Dis., 2011, 1:15-23.

Spasticity can be incapacitating and can be triggered at any time through a variety of stimuli. External factors such as constipation, urinary tract infections, and pressure ulcers may exacerbate spasticity and its symptoms. Kischka U., Medicine, 2008 36:616-9. Spasticity can also have functionally limiting and painful sequelae, including diminished joint mobility, decreased muscle flexibility, and sleep disorders secondary to airway obstruction. Left untreated, spasticity may lead to deformities, such as kyphoscoliosis and contractures, which can be difficult to correct. Chang, supra.

Existing therapeutics used to treat spasticity include centrally acting agents such as baclofen, clonidine, and tizanidine, anticonvulsants such as benzodiazepines and gabapentin, and peripherally acting agents such as dantrolene. Each of these therapeutics is attended by adverse effects. Id. For example, adverse effects of baclofen, a GABA B agonist used as a first-line treatment for spasticity, include systemic muscle relaxation, sedation, and fatigue. Chou R. et al., J Pain Symptom Manage., 2004, 28:140-75. Because of potential hepatotoxicity, liver function should be monitored with baclofen use. Oral baclofen is not recommended for elderly patients because of excessive drowsiness. Furthermore, caution should be taken when treating patients in the recovery phase of brain injury because there has been some evidence of deleterious effects on brain plasticity. Withdrawing baclofen treatment has been associated with hyperthermia, seizures, and altered mental status. Chang, supra.

Alpha-2 agonists used to treat spasticity include clonidine and tizanidine. Clonidine is rarely used as a single agent in the treatment of spasticity because of adverse effects that include hypotension, bradycardia, and drowsiness. Rabchevsky A G, Kitzman P H., Neurotherapeutics 2011, 8:274-82. Tizanidine, which is often used in conjunction with other oral drugs such as baclofen, requires frequent dosing due to its short half-life and may be attended by adverse effects that include sedation, hypotension, xerostomia, muscle weakness, and hallucinations. Tizanidine is contraindicated in patients taking hypertension medication, and has been known to prolong the QT interval. Chang, supra.

Anticonvulsants used to treat spasticity are also attended by a variety of adverse effects. For example, diazepam and clonazepam cause significant sedation, and their long-term use can lead to dependence and increased tolerance. Gabapentin, which is typically not used as a first-line treatment, may somnolence, tremor, and nystagm. Lapeyre E. et al., Neuro Rehabilitation, 2010, 27:193-200.

While skilled physicians will often vary the type of drug and dosing used to treat a patient's spasticity, a need clearly exists for new methods of treatment, particularly for ones that avoid the adverse effects and addiction dangers associated with existing medications.

SUMMARY OF THE INVENTION

This invention is based on the discovery that spasticity can be reduced by inhibiting adaptor associated kinase 1 (AAK1). Thus, one embodiment of the invention encompasses a method of treating or preventing spasticity which comprises inhibiting adaptor associated kinase 1 (AAK1) in a patient in need thereof. Another embodiment encompasses a method of treating or preventing spasticity which comprises administering a therapeutically or prophylactically effective amount of an AAK1 inhibitor to a patient in need thereof.

In certain embodiments of the invention, the patient suffers from spinal cord injury, cerebral palsy, stroke, amyotrophic lateral sclerosis, or multiple sclerosis.

In certain embodiments, the AAK1 inhibitor is a compound of Formula (I):

(I)

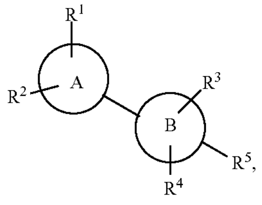

or a pharmaceutically acceptable salt thereof, wherein:

A is selected from

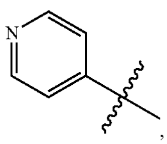
,
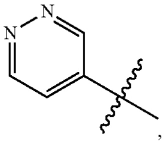
,
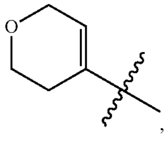
,
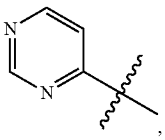
,

-continued

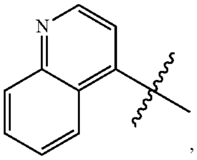
,
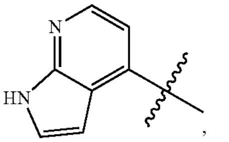
,
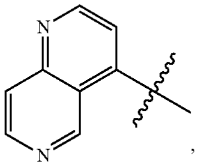
, and
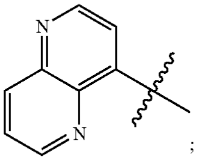
;

wherein  denotes the point of attachment to B;

B is selected from

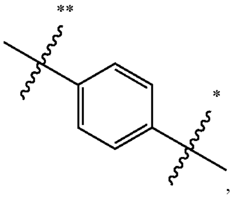
,
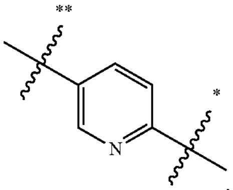
,
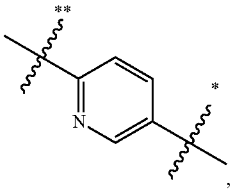
,
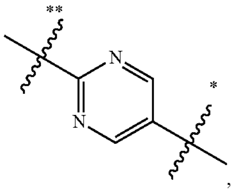
,
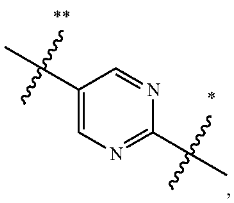
, and
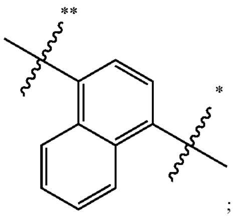
;

and wherein "*" indicates the point of attachment to $R^5$ and "**" indicates the point of attachment to ring A;

$R^1$ is selected from hydrogen, amino, —$CO_2H$, difluoromethyl, ethyl, halo, hydroxymethyl, methoxy, methyl, —$NHC(O)CH_3$, —$NHCO_2CH_3$, trifluoromethoxy, and trifluoromethyl;

$R^2$ is selected from hydrogen, cyano, —$CH_2OH$, halo, and methyl;

$R^3$ is selected from hydrogen, cyano, cyclopropyl, difluoromethyl, halo, hydroxymethyl, methoxy, methyl, methylsulfonyl, trifluoromethoxy, trifluoromethyl, —$CH_2N(CH_3)_2$, and a five-membered aromatic ring containing one, two, or three heteroatoms selected from nitrogen, oxygen, and sulfur;

$R^4$ is selected from hydrogen, halo, and methyl;

$R^5$ is selected from

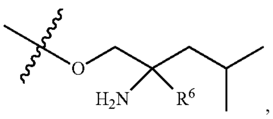
,

-continued

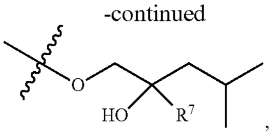
, and
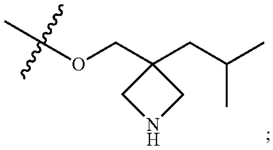
;

$R^6$ is selected from hydrogen, ethyl, fluoromethyl, difluoromethyl, methyl, and trifluoromethyl; and $R^7$ is methyl.

In some embodiments, the AAK1 inhibitor is a compound of Formula (11):

(II)

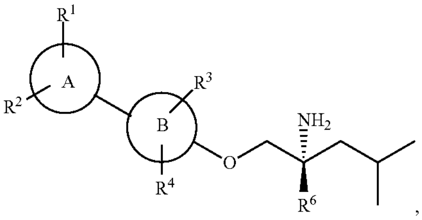
, or a pharmaceutically acceptable salt thereof, wherein:

A is selected from

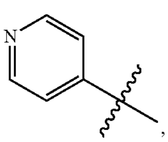
,
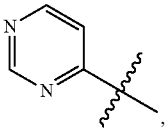
,
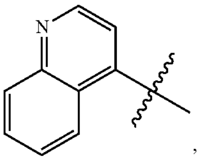
,
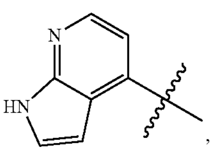
,
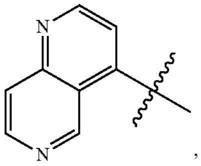
, and
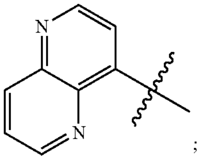
;

and wherein "" denotes the point of attachment to B;

B is selected from phenyl and pyridinyl;

$R^1$ is selected from hydrogen, difluoromethyl, halo, methoxy, methyl, —$NHC(O)CH_3$, —$NHCO_2CH_3$, and trifluoromethyl;

$R^2$ is selected from hydrogen, —$CH_2OH$, and halo;

$R^3$ is selected from hydrogen, cyano, cyclopropyl, difluoromethyl, halo, hydroxymethyl, methoxy, methyl, trifluoromethoxy, trifluoromethyl, and a five-membered aromatic ring containing one, two, or three heteroatoms selected from nitrogen, oxygen, and sulfur;

$R^4$ is selected from hydrogen, halo, and methyl; and $R^6$ is selected from hydrogen, ethyl, fluoromethyl, difluoromethyl, methyl, and trifluoromethyl.

In certain embodiments of the invention, A is

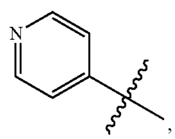

,

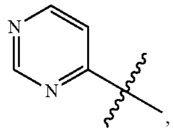

, and

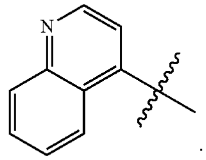

.

In certain embodiments, B is

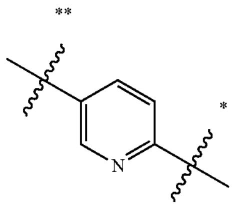

and

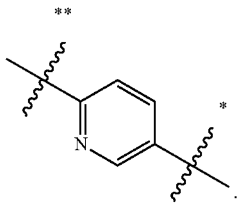

.

In certain embodiments, $R^5$ is

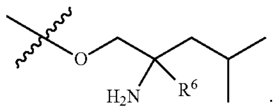

.

A specific embodiment of the invention encompasses a method of treating or preventing spasticity which comprises administering a therapeutically or prophylactically effective amount of an adaptor associated kinase 1 (AAK1) inhibitor to a patient in need thereof, wherein the AAK1 inhibitor is (S)-1-((2',6-bis(difluoromethyl)-[2,4'-bipyridin]-5-yl)oxy)-2,4-dimethylpentan-2-amine:

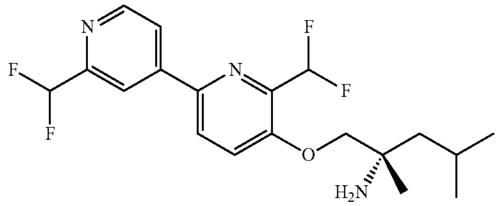 [SMILES: CC(C)C[C@](C)(N)COc1ccc(-c2ccnc(C(F)F)c2)nc1C(F)F]

or a pharmaceutically acceptable salt thereof. One particular salt is ((S)-1-((2',6-bis(difluoromethyl)-[2,4'-bipyridin]-5-yl)oxy)-2,4-dimethylpentan-2-aminium dihydrogen phosphate, which may be administered orally.

DESCRIPTION OF DRAWINGS

Aspects of this invention may be better understood by reference to one or more of the following drawings.

DETAILED DESCRIPTION OF THE INVENTION

Figure 1:
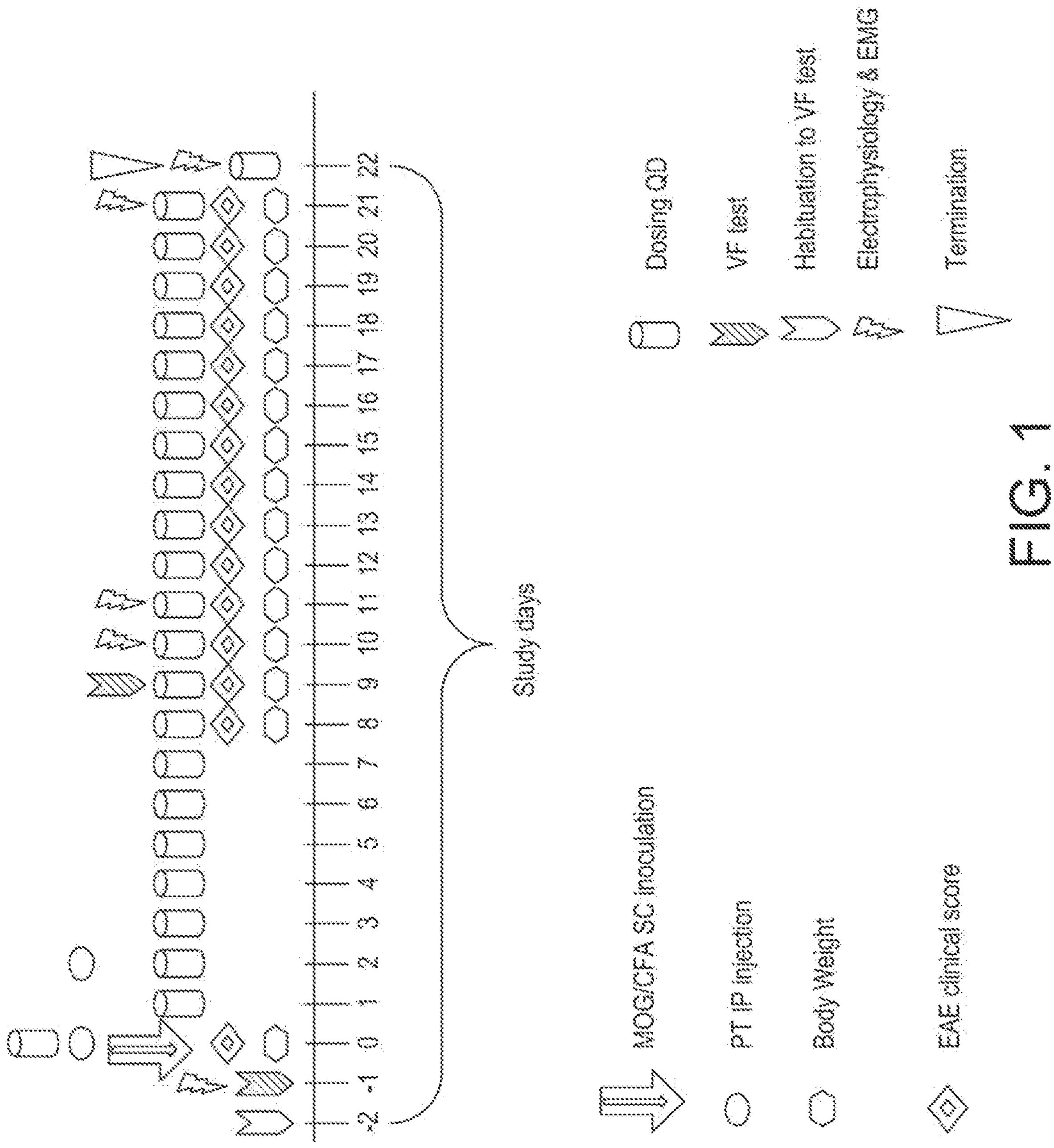
FIG. 1 provides a schematic depiction of the myelin oligodendrocyte glycoprotein (MOG)-induced murine model of experimental autoimmune encephalomyelitis (EAE) used herein.

This invention is based on the discovery that the inhibition of adaptor associated kinase 1 (AAK1) (e.g., by the administration of a centrally-acting AAK1 inhibitor) can reduce spasticity in established animal models.

Adaptor associated kinase 1 is a member of the Ark1/Prk1 family of serine/threonine kinases. Recently, a number of AAK1 inhibitors have been disclosed that may be useful in the treatment of neuropathic pain. See, e.g., U.S. Pat. No. 9,902,722; Hartz, R. A., et al., J. Med. Chem., 2021 Aug. 12:64(15):11090-11128; Luo G., et al., J Med Chem. 2022 Mar. 24; 65(6):4534-4564; and Luo G, et al., J Med Chem. 2022 Mar. 24; 65(6):4457-4480. However, the mechanism by which the compounds exhibit their pharmacological effect remains unclear. Much work remains to be done before those in the art fully understand how AAK1 inhibition can decrease neuropathic pain.

Definitions

In describing and claiming the disclosed subject matter, the following terminology will be used in accordance with the definitions set forth below.

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, the terms “prevent,” “preventing” and “prevention” contemplate an action that occurs before a patient begins to suffer from the specified disease or disorder, which inhibits or reduces the severity of the disease or disorder. In other words, the terms encompass prophylaxis.

Unless otherwise indicated, a “prophylactically effective amount” of a compound is an amount sufficient to prevent a disease or condition, or one or more symptoms associated with the disease or condition, or prevent its recurrence. A “prophylactically effective amount” of a compound means an amount of therapeutic agent, alone or in combination with other agents, which provides a prophylactic benefit in the prevention of the disease. The term “prophylactically effective amount” can encompass an amount that improves overall prophylaxis or enhances the prophylactic efficacy of another prophylactic agent.

Unless otherwise indicated, a “therapeutically effective amount” of a compound is an amount sufficient to provide a therapeutic benefit in the treatment or management of a disease or condition, or to delay or minimize one or more symptoms associated with the disease or condition. A “therapeutically effective amount” of a compound means an amount of therapeutic agent, alone or in combination with other therapies, that provides a therapeutic benefit in the treatment or management of the disease or condition. The term “therapeutically effective amount” can encompass an amount that improves overall therapy, reduces or avoids symptoms or causes of a disease or condition, or enhances the therapeutic efficacy of another therapeutic agent.

Unless otherwise indicated, the terms “treat,” “treating” and “treatment” contemplate an action that occurs while a patient is suffering from the specified disease or disorder, which reduces the severity of the disease or disorder, or retards or slows the progression of the disease or disorder. As used herein, the term encompasses the management of a disease or disorder.

As used herein, the singular forms “a”, “an”, and “the” include plural reference unless the context clearly dictates otherwise.

Unless otherwise indicated, the term “about” is used herein to mean within the typical ranges of tolerances in the art. For example, “about” can be understood as about 2 standard deviations from the mean. In certain embodiments, about means±10%. In certain embodiments, about means 5%. When about is present before a series of numbers or a range, it is understood that “about” can modify each of the numbers in the series or range.

AAK1 Inhibitors

This invention encompasses methods of using and compositions comprising adaptor associated kinase 1 (AAK1) inhibitors disclosed in U.S. Pat. No. 9,902,722. Particular compounds include those of formula (I):

(I)

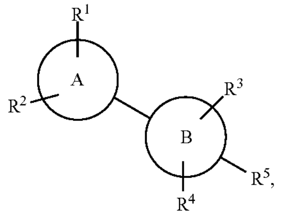

and pharmaceutically acceptable salts thereof, wherein:

A is selected from

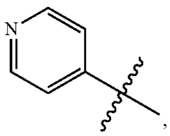,
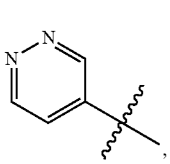,
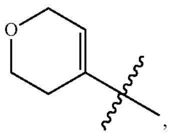,
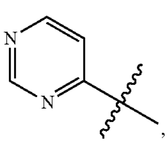,
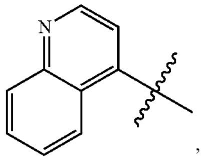,
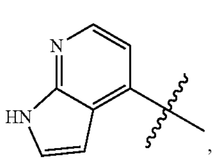,
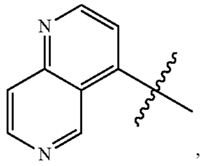, and
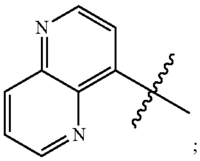;

wherein “ ” denotes the point of attachment to B;

B is selected from

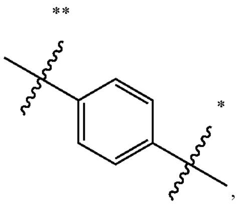,
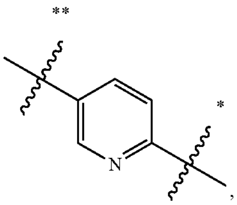,
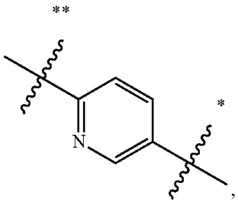,
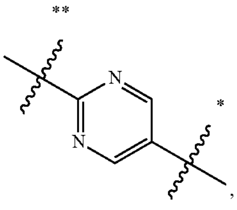,

-continued

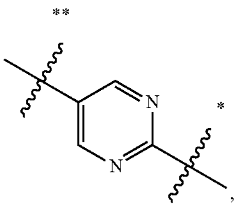

, and

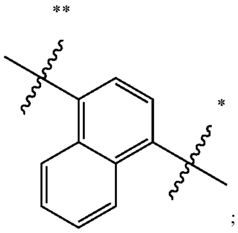

;

wherein "*" indicates the point of attachment to $R^5$ and "**" indicates the point of attachment to ring A;

$R^1$ is selected from hydrogen, amino, —$CO_2H$, difluoromethyl, ethyl, halo, hydroxymethyl, methoxy, methyl, —$NHC(O)CH_3$, —$NHCO_2CH_3$, trifluoromethoxy, and trifluoromethyl;

$R^2$ is selected from hydrogen, cyano, —$CH_2OH$, halo, and methyl;

$R^3$ is selected from hydrogen, cyano, cyclopropyl, difluoromethyl, halo, hydroxymethyl, methoxy, methyl, methylsulfonyl, trifluoromethoxy, trifluoromethyl, —$CH_2N(CH_3)_2$, and a five-membered aromatic ring containing one, two, or three heteroatoms selected from nitrogen, oxygen, and sulfur;

$R^4$ is selected from hydrogen, halo, and methyl;

$R^5$ is selected from

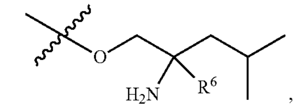

,

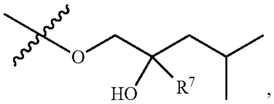

, and

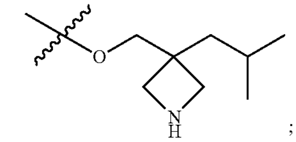

;

$R^6$ is selected from hydrogen, ethyl, fluoromethyl, difluoromethyl, methyl, and trifluoromethyl; and $R^7$ is methyl.

In some embodiments of formula (I), A is selected from

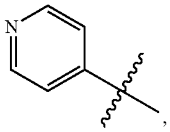

,

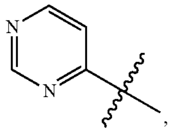

, and

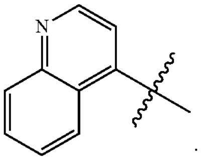

.

In some embodiments of formula (I), B is selected from

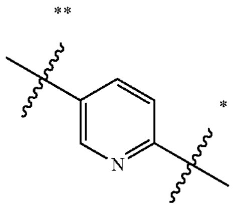

and

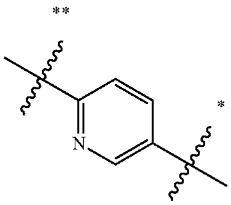

.

In some embodiments of formula (I), B is:

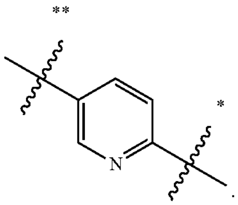 [SMILES: *c1ccc(*)nc1]

.

In some embodiments of formula (I), $R^5$ is

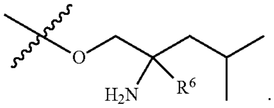

.

Particular AAK1 inhibitors include those of formula (II):

(II)

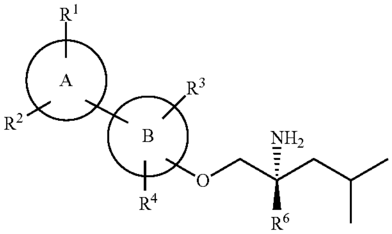

and pharmaceutically acceptable salts thereof, wherein:

A is selected from

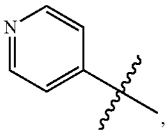

,

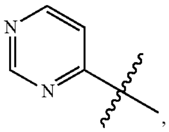

,

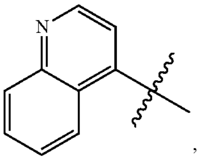

,

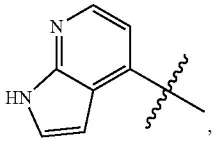

,

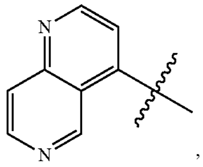

, and

-continued

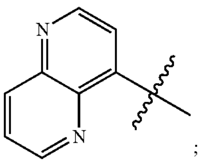

;

Wherein "" denotes the point of attachment to B; 

B is selected from phenyl and pyridinyl;

$R^1$ is selected from hydrogen, difluoromethyl, halo, methoxy, methyl, —NHC(O)$CH_3$, —$NHCO_2CH_3$, and trifluoromethyl;

$R^2$ is selected from hydrogen, —$CH_2OH$, and halo;

$R^3$ is selected from hydrogen, cyano, cyclopropyl, difluoromethyl, halo, hydroxymethyl, methoxy, methyl, trifluoromethoxy, trifluoromethyl, and a five-membered aromatic ring containing one, two, or three heteroatoms selected from nitrogen, oxygen, and sulfur;

$R^4$ is selected from hydrogen, halo, and methyl; and $R^5$ is selected from hydrogen, ethyl, fluoromethyl, difluoromethyl, methyl, and trifluoromethyl.

In some embodiments of formula (II), A is selected from

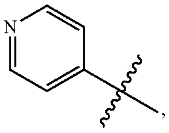

,

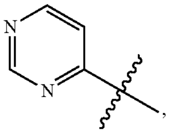

, and

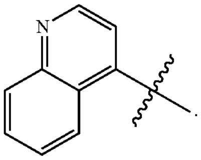

.

In some embodiments of formula (II), B is pyridinyl.

In some embodiments of formula (II), B is:

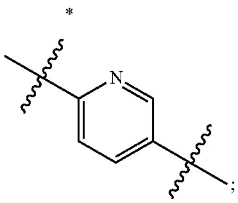 [SMILES: *c1ccc(*)nc1]

;

wherein "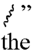" denotes the point of attachment to A and "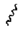" denotes the point of  attachment to the oxygen atom.

In some embodiments of formula (11), A is selected from

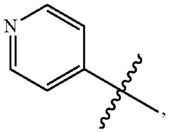

,

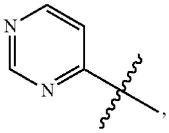

, and

-continued

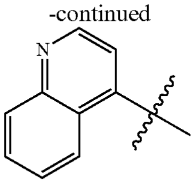

B is

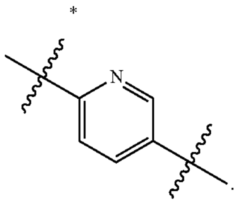 [SMILES: *c1ccc(*)nc1]

.

Specific AAK1 inhibitors include:

(S)—N-(4-(4-((2-amino-4-methylpentyl)oxy)-3-fluorophenyl)pyridin-2-yl)acetamide;

(S)—N-(4-(4-((2-amino-4-methylpentyl)oxy)-3-methoxyphenyl)pyridin-2-yl)acetamide;

(S)—N-(4-(4-((2-amino-4-methylpentyl)oxy)-3-cyanophenyl)pyridin-2-yl)acetamide;

(S)-2-((2-amino-4-methylpentyl)oxy)-5-(2-aminopyridin-4-yl)benzonitrile;

(S)—N-(4-(4-((2-amino-4-methylpentyl)oxy)-3-(trifluoromethyl)phenyl)pyridin-2-yl)acetamide;

(S)—N-(4-(4-((2-amino-4-methylpentyl)oxy)-3-(trifluoromethoxy)phenyl)pyridin-2-yl)acetamide;

(S)—N-(4-(4-((2-amino-4-methylpentyl)oxy)-3-methylphenyl)pyridin-2-yl)acetamide;

(S)—N-(4-(4-((2-amino-4-methylpentyl)oxy)-3-chlorophenyl)pyridin-2-yl)acetamide;

(S)—N-(4-(4-((2-amino-4-methylpentyl)oxy)-3,5-difluorophenyl)pyridin-2-yl)acetamide;

(S)—N-(4-(4-((2-amino-4-methylpentyl)oxy)-3-chloro-5-fluorophenyl)pyridin-2-yl)acetamide;

(S)—N-(4-(4-((2-amino-4-methylpentyl)oxy)-3-fluoro-5-(trifluoromethyl)phenyl)pyridin-2-yl)acetamide;

(S)—N-(4-(4-((2-amino-4-methylpentyl)oxy)-2,5-difluorophenyl)pyridin-2-yl)acetamide;

(S)-methyl (4-(4-((2-amino-4-methylpentyl)oxy)-3-fluorophenyl)pyridin-2-yl)carbamate;

(S)-methyl (4-(4-((2-amino-4-methylpentyl)oxy)-3-(isoxazol-5-yl)phenyl)pyridin-2-yl)carbamate;

(S)-2-((2-amino-4-methylpentyl)oxy)-5-(2-methylpyridin-4-yl)benzonitrile;

(S)-2-((2-amino-4-methylpentyl)oxy)-5-(2-methoxypyridin-4-yl)benzonitrile;

(S)-2-((2-amino-4-methylpentyl)oxy)-5-(2-(trifluoromethyl)pyridin-4-yl)benzonitrile;

(S)-1-(2-(isoxazol-5-yl)-4-(2-methylpyridin-4-yl)phenoxy)-4-methylpentan-2-amine;

(S)—N-(4-(4-((2-amino-2,4-dimethylpentyl)oxy)-3-(trifluoromethyl)phenyl)pyridin-2-yl)acetamide;

(S)-methyl (4-(4-((2-amino-2,4-dimethylpentyl)oxy)-3-(trifluoromethyl)phenyl)pyridin-2-yl)carbamate;

(S)—N-(4-(4-((2-amino-2,4-dimethylpentyl)oxy)-3-cyanophenyl)pyridin-2-yl)acetamide;

(S)-methyl (4-(4-((2-amino-2,4-dimethylpentyl)oxy)-3-cyanophenyl)pyridin-2-yl)carbamate;

(S)—N-(4-(4-((2-amino-2,4-dimethylpentyl)oxy)-3-(difluoromethyl)phenyl)pyridin-2-yl)acetamide;
(S)-methyl (4-(4-((2-amino-2,4-dimethylpentyl)oxy)-3-(difluoromethyl)phenyl)pyridin-2-yl)carbamate;
(S)—N-(4-(4-((2-amino-2,4-dimethylpentyl)oxy)-3-(trifluoromethoxy)phenyl)pyridin-2-yl)acetamide;
(S)-methyl (4-(4-((2-amino-2,4-dimethylpentyl)oxy)-3-(trifluoromethoxy)phenyl)pyridin-2-yl)carbamate;
(S)—N-(4-(4-((2-amino-2,4-dimethylpentyl)oxy)-3-fluorophenyl)pyridin-2-yl)acetamide;
(S)-methyl (4-(4-((2-amino-2,4-dimethylpentyl)oxy)-3-fluorophenyl)pyridin-2-yl)carbamate;
methyl (4-(4-((2-amino-2,4-dimethylpentyl)oxy)-3-chlorophenyl)pyridin-2-yl)carbamate;
methyl (4-(4-((2-amino-2,4-dimethylpentyl)oxy)-3-methylphenyl)pyridin-2-yl)carbamate;
methyl (4-(4-((2-amino-2,4-dimethylpentyl)oxy)-2,3-dimethylphenyl)pyridin-2-yl)carbamate;
(S)-methyl (4-(4-((2-amino-2,4-dimethylpentyl)oxy)-3-(hydroxymethyl)phenyl)pyridin-2-yl)carbamate;
(S)-methyl (4-(4-((2-amino-2,4-dimethylpentyl)oxy)-3-cyclopropylphenyl)pyridin-2-yl)carbamate;
(S)—N-(4-(4-((2-amino-2,4-dimethylpentyl)oxy)-3-(trifluoromethyl)phenyl)-5-(hydroxymethyl)pyridin-2-yl)acetamide;
(S)-1-(4-(2-(difluoromethyl)pyridin-4-yl)-2-(trifluoromethyl)phenoxy)-2,4-dimethylpentan-2-amine;
(S)-2-((2-amino-2,4-dimethylpentyl)oxy)-5-(2-(difluoromethyl)pyridin-4-yl)benzonitrile;
(S)-1-(2-(difluoromethyl)-4-(2-(difluoromethyl)pyridin-4-yl)phenoxy)-2,4-dimethylpentan-2-amine;
(S)-1-(4-(2-(difluoromethyl)pyridin-4-yl)-2-(trifluoromethoxy)phenoxy)-2,4-dimethylpentan-2-amine;
(S)-1-(4-(3-chloro-2-fluoropyridin-4-yl)-2-(trifluoromethyl)phenoxy)-2,4-dimethylpentan-2-amine;
(S)-1-(4-(5-chloro-2-fluoropyridin-4-yl)-2-(trifluoromethyl)phenoxy)-2,4-di methylpentan-2-amine;
(S)-1-(4-(2-fluoro-3-methylpyridin-4-yl)-2-(trifluoromethyl)phenoxy)-2,4-dimethylpentan-2-amine;
(S)-1-(4-(2,3-difluoropyridin-4-yl)-2-(trifluoromethyl)phenoxy)-2,4-dimethylpentan-2-amine;
(S)-2,4-dimethyl-1-(4-(pyridin-4-yl)-2-(trifluoromethyl)phenoxy)pentan-2-amine;
(S)-1-(4-(2-fluoropyridin-4-yl)-2-(trifluoromethyl)phenoxy)-2,4-dimethylpentan-2-amine;
(S)-2,4-dimethyl-1-(4-(2-methylpyridin-4-yl)-2-(trifluoromethyl)phenoxy)pentan-2-amine;
(S)-1-(4-(3-methoxypyridin-4-yl)-2-(trifluoromethyl)phenoxy)-2,4-dimethylpentan-2-amine;
(S)-1-(4-(3-fluoropyridin-4-yl)-2-(trifluoromethyl)phenoxy)-2,4-dimethylpentan-2-amine;
(S)-2-((2-amino-2,4-dimethylpentyl)oxy)-5-(2-methylpyridin-4-yl)benzonitrile;
(S)-1-(2-cyclopropyl-4-(2-methylpyridin-4-yl)phenoxy)-2,4-dimethylpentan-2-amine;
(S)-1-(2-(difluoromethyl)-4-(2-methylpyridin-4-yl)phenoxy)-2,4-dimethylpentan-2-amine;
methyl (6-((2-amino-2,4-dimethylpentyl)oxy)-[3,4'-bipyridin]-2'-yl)carbamate;
(S)-methyl (6-((2-amino-2,4-dimethylpentyl)oxy)-5-methyl-[3,4'-bipyridin]-2'-yl)carbamate;
(S)-methyl (6-((2-amino-2,4-dimethylpentyl)oxy)-5-cyano-[3,4'-bipyridin]-2'-yl)carbamate;
(S)-methyl (6-((2-amino-2,4-dimethylpentyl)oxy)-4-methyl-[3,4'-bipyridin]-2'-yl)carbamate;
(S)-methyl (6-((2-amino-2,4-dimethylpentyl)oxy)-5-chloro-[3,4'-bipyridin]-2'-yl)carbamate;
(S)-methyl (6-((2-amino-2,4-dimethylpentyl)oxy)-5-methoxy-[3,4'-bipyridin]-2'-yl)carbamate;
(S)-1-((2'-chloro-5-methyl-[3,4'-bipyridin]-6-yl)oxy)-2,4-dimethylpentan-2-amine;
(S)-1-((2'-(difluoromethyl)-5-methyl-[3,4'-bipyridin]-6-yl)oxy)-2,4-dimethylpentan-2-amine;
(S)-6-((2-amino-2,4-dimethylpentyl)oxy)-2'-(difluoromethyl)-[3,4'-bipyridine]-5-carbonitrile;
(S)-1-((5-chloro-2'-methyl-[3,4'-bipyridin]-6-yl)oxy)-2,4-dimethylpentan-2-amine;
(S)-1-((2',5-dimethyl-[3,4'-bipyridin]-6-yl)oxy)-2,4-dimethylpentan-2-amine;
(S)-1-((5-methoxy-2'-methyl-[3,4'-bipyridin]-6-yl)oxy)-2,4-dimethylpentan-2-amine;
methyl (5-((2-amino-2,4-dimethylpentyl)oxy)-[2,4'-bipyridin]-2'-yl)carbamate;
(S)-methyl (5-((2-amino-2,4-dimethylpentyl)oxy)-6-methyl-[2,4'-bipyridin]-2'-yl)carbamate;
(S)-1-((2',6-dimethyl-[2,4'-bipyridin]-5-yl)oxy)-2,4-dimethylpentan-2-amine;
(S)-methyl (5-((2-amino-2,4-dimethylpentyl)oxy)-6-chloro-[2,4'-bipyridin]-2'-yl)carbamate;
(S)-1-((6-chloro-2'-methyl-[2,4'-bipyridin]-5-yl)oxy)-2,4-dimethylpentan-2-amine;
(S)-methyl (5-((2-amino-2,4-dimethylpentyl)oxy)-4-methyl-[2,4'-bipyridin]-2'-yl)carbamate;
(S)-2,4-dimethyl-1-(4-(quinolin-4-yl)-2-(trifluoromethyl)phenoxy)pentan-2-amine;
(S)-2,4-dimethyl-1-(2-(trifluoromethyl)-4-(7-(trifluoromethyl)quinolin-4-yl)phenoxy)pentan-2-amine;
(S)-1-(4-(7-fluoroquinolin-4-yl)-2-(trifluoromethyl)phenoxy)-2,4-dimethylpentan-2-amine;
(S)-1-(4-(5,7-difluoroquinolin-4-yl)-2-(trifluoromethyl)phenoxy)-2,4-dimethylpentan-2-amine;
(S)-1-(4-(6-fluoroquinolin-4-yl)-2-(trifluoromethyl)phenoxy)-2,4-dimethylpentan-2-amine;
(S)-1-(2-cyclopropyl-4-(quinolin-4-yl)phenoxy)-2,4-dimethylpentan-2-amine;
1-(2-chloro-6-fluoro-4-(quinolin-4-yl)phenoxy)-2,4-dimethylpentan-2-amine;
(S)-1-((5-(7-fluoroquinolin-4-yl)-3-methylpyridin-2-yl)oxy)-2,4-dimethylpentan-2-amine;
(S)-2-((2-amino-2,4-dimethylpentyl)oxy)-5-(5,7-difluoroquinolin-4-yl)nicotinonitrile;
(S)-1-((3-chloro-5-(quinolin-4-yl)pyridin-2-yl)oxy)-2,4-dimethylpentan-2-amine;
(S)-1-((3-methoxy-5-(quinolin-4-yl)pyridin-2-yl)oxy)-2,4-dimethylpentan-2-amine;
(S)-2-((2-amino-2,4-dimethylpentyl)oxy)-5-(1,6-naphthyridin-4-yl)nicotinonitrile;
(S)-2,4-dimethyl-1-((2-methyl-6-(quinolin-4-yl)pyridin-3-yl)oxy)pentan-2-amine;
(S)-2,4-dimethyl-1-((4-methyl-6-(quinolin-4-yl)pyridin-3-yl)oxy)pentan-2-amine;
(S)-1-((2-chloro-6-(quinolin-4-yl)pyridin-3-yl)oxy)-2,4-dimethylpentan-2-amine;
(S)-1-(4-(1H-pyrrolo[2,3-b]pyridin-4-yl)-2-(trifluoromethyl)phenoxy)-2,4-dimethylpentan-2-amine;
(S)-1-(4-(1,6-naphthyridin-4-yl)-2-(trifluoromethyl)phenoxy)-2,4-dimethylpentan-2-amine;
(S)-2-((2-amino-2,4-dimethylpentyl)oxy)-5-(1,6-naphthyridin-4-yl)benzonitrile;
(S)-2-((2-amino-2,4-dimethylpentyl)oxy)-5-(1,5-naphthyridin-4-yl)benzonitrile;
(S)-1-(4-(7-chloroquinolin-4-yl)-2-(trifluoromethyl)phenoxy)-2,4-dimethylpentan-2-amine;

(S)-4-(4-((2-amino-2,4-dimethylpentyl)oxy)-3-(trifluoromethyl)phenyl)quinoline-7-carbonitrile;
(S)-2,4-dimethyl-1-(2-methyl-4-(2-methylpyridin-4-yl)phenoxy)pentan-2-amine;
(S)-1-(2-fluoro-4-(2-methylpyridin-4-yl)phenoxy)-2,4-dimethylpentan-2-amine;
(S)-1-(4-(2-fluoropyridin-4-yl)-2-methylphenoxy)-2,4-dimethylpentan-2-amine;
(S)-1-(2-fluoro-4-(2-fluoropyridin-4-yl)phenoxy)-2,4-dimethylpentan-2-amine;
(S)-2-((2-amino-2,4-dimethylpentyl)oxy)-5-(2-fluoropyridin-4-yl)benzonitrile;
(S)-1-((2'-fluoro-5-methyl-[3,4'-bipyridin]-6-yl)oxy)-2,4-dimethylpentan-2-amine;
(S)-4-(6-((2-amino-2,4-dimethylpentyl)oxy)-5-methylpyridin-3-yl)quinoline-7-carbonitrile;
(S)-1-((5-fluoro-2'-methyl-[3,4'-bipyridin]-6-yl)oxy)-2,4-dimethylpentan-2-amine;
(S)-1-((3-fluoro-5-(quinolin-4-yl)pyridin-2-yl)oxy)-2,4-dimethylpentan-2-amine;
(S)-4-(6-((2-amino-2,4-dimethylpentyl)oxy)-5-fluoropyridin-3-yl)quinoline-7-carbonitrile;
(S)-methyl (4-(4-((2-amino-2,4-dimethylpentyl)oxy)-3-cyanophenyl)-3-fluoropyridin-2-yl)carbamate;
(S)-6-((2-amino-2,4-dimethylpentyl)oxy)-2'-methyl-[3,4'-bipyridine]-5-carbonitrile;
(S)-2-((2-amino-2,4-dimethylpentyl)oxy)-5-(7-methylquinolin-4-yl)benzonitrile;
(S)-2-((2-amino-2,4-dimethylpentyl)oxy)-5-(3-fluoro-2-methylpyridin-4-yl)benzonitrile;
(S)-2-((2-amino-2,4-dimethylpentyl)oxy)-5-(quinolin-4-yl)benzonitrile;
(S)-2-((2-amino-2,4-dimethylpentyl)oxy)-5-(5-fluoro-2-methylpyridin-4-yl)benzonitrile;
(S)-methyl (4-(4-((2-amino-2,4-dimethylpentyl)oxy)-3-cyanophenyl)-5-fluoropyridin-2-yl carbamate;
(S)-1-((6-fluoro-2',4-dimethyl-[2,4'-bipyridin]-5-yl)oxy)-2,4-dimethylpentan-2-amine;
methyl (5-((3-isobutylazetidin-3-yl)methoxy)-6-methyl-[2,4'-bipyridin]-2'-yl)carbamate;
(S)-2-((2-amino-4-methylpentyl)oxy)-5-(6-methylpyridazin-4-yl)benzonitrile;
(S)-1-(2-(isoxazol-5-yl)-4-(quinolin-4-yl)phenoxy)-4-methylpentan-2-amine;
(S)-4-(4-((2-amino-2,4-dimethylpentyl)oxy)-3-(trifluoromethyl)phenyl)-2-methylnicotinic acid;
(S)-methyl (4-(4-((2-amino-2,4-dimethylpentyl)oxy)-3-((dimethylamino)methyl)phenyl)pyridin-2-yl)carbamate;
(S)-methyl (4-(4-((2-amino-2,4-dimethylpentyl)oxy)-3-(methylsulfonyl)phenyl)pyridin-2-yl)carbamate;
(S)-2,4-dimethyl-1-(4-(2-methylpyridin-4-yl)-2-(methylsulfonyl)phenoxy)pentan-2-amine;
(S)-2,4-dimethyl-1-(2-(methylsulfonyl)-4-(quinolin-4-yl)phenoxy)pentan-2-amine;
(S)-1-(2-(difluoromethyl)-4-(6-fluoroquinolin-4-yl)phenoxy)-2,4-dimethylpentan-2-amine;
(S)-methyl (5-((2-amino-2,4-dimethylpentyl)oxy)-6-(difluoromethyl)-[2,4'-bipyridin]-2'-yl)carbamate;
(S)-1-((2-(difluoromethyl)-6-(quinolin-4-yl)pyridin-3-yl)oxy)-2,4-dimethylpentan-2-amine;
(S)-1-((6-(difluoromethyl)-2'-methyl-[2,4'-bipyridin]-5-yl)oxy)-2,4-dimethylpentan-2-amine;
(S)-methyl (5-((2-amino-2,4-dimethylpentyl)oxy)-4-(difluoromethyl)-[2,4'-bipyridin]-2'-yl)carbamate;
(S)-1-((4-(difluoromethyl)-6-(quinolin-4-yl)pyridin-3-yl)oxy)-2,4-dimethylpentan-2-amine;
(S)-1-((4-(difluoromethyl)-2'-methyl-[2,4'-bipyridin]-5-yl)oxy)-2,4-dimethylpentan-2-amine;
(S)-1-((2',6-bis(difluoromethyl)-[2,4'-bipyridin]-5-yl)oxy)-2,4-dimethylpentan-2-amine;
(S)-1-((2',4-bis(difluoromethyl)-[2,4'-bipyridin]-5-yl)oxy)-2,4-dimethylpentan-2-amine;
(S)-1-((2'-(difluoromethyl)-4-methyl-[2,4'-bipyridin]-5-yl)oxy)-2,4-dimethylpentan-2-amine;
(S)-1-(2-cyclopropyl-4-(2-(difluoromethyl)pyridin-4-yl)phenoxy)-2,4-dimethylpentan-2-amine;
(S)-1-((2-(difluoromethyl)-6-(6-fluoroquinolin-4-yl)pyridin-3-yl)oxy)-2,4-dimethylpentan-2-amine;
(S)-1-((2-(difluoromethyl)-6-(7-fluoroquinolin-4-yl)pyridin-3-yl)oxy)-2,4-dimethylpentan-2-amine;
(S)-1-((2-(difluoromethyl)-6-(5,7-difluoroquinolin-4-yl)pyridin-3-yl)oxy)-2,4-dimethylpentan-2-amine;
(S)-1-((4-(difluoromethyl)-6-(5,7-difluoroquinolin-4-yl)pyridin-3-yl)oxy)-2,4-dimethylpentan-2-amine;
(S)-1-((4-(difluoromethyl)-6-(7-fluoroquinolin-4-yl)pyridin-3-yl)oxy)-2,4-dimethylpentan-2-amine;
(S)-1-((4-(difluoromethyl)-6-(6-fluoroquinolin-4-yl)pyridin-3-yl)oxy)-2,4-dimethylpentan-2-amine;
((S)-1-((4-(difluoromethyl)-6-(6-(trifluoromethyl)quinolin-4-yl)pyridin-3-yl)oxy)-2,4-dimethylpentan-2-amine;
(S)-1-((4-(difluoromethyl)-6-(6-(trifluoromethoxy)quinolin-4-yl)pyridin-3-yl)oxy)-2,4-dimethylpentan-2-amine;
(S)-1-((2-chloro-6-(5,7-difluoroquinolin-4-yl)pyridin-3-yl)oxy)-2,4-dimethylpentan-2-amine;
(S)-1-((2-chloro-6-(7-fluoroquinolin-4-yl)pyridin-3-yl)oxy)-2,4-dimethylpentan-2-amine;
(S)-1-((6-(7-fluoroquinolin-4-yl)-2-methylpyridin-3-yl)oxy)-2,4-dimethylpentan-2-amine;
(S)-1-((6-(6-fluoroquinolin-4-yl)-2-methylpyridin-3-yl)oxy)-2,4-dimethylpentan-2-amine;
(S)-1-((2-(difluoromethyl)-6-(2-methylpyrimidin-4-yl)pyridin-3-yl)oxy)-2,4-dimethylpentan-2-amine;
(S)-1-((2-(difluoromethyl)-6-(6-methylpyrimidin-4-yl)pyridin-3-yl)oxy)-2,4-dimethylpentan-2-amine;
(S)-1-((4-(difluoromethyl)-2'-ethyl-[2,4'-bipyridin]-5-yl)oxy)-2,4-dimethylpentan-2-amine;
(S)-1-((2'-chloro-4-(difluoromethyl)-3'-fluoro-[2,4'-bipyridin]-5-yl)oxy)-2,4-dimethylpentan-2-amine;
(S)-1-((2'-chloro-4-(difluoromethyl)-5'-fluoro-[2,4'-bipyridin]-5-yl)oxy)-2,4-dimethylpentan-2-amine;
(S)-2,4-dimethyl-1-((2'-methyl-4-(trifluoromethyl)-[2,4'-bipyridin]-5-yl)oxy)pentan-2-amine;
(S)-2,4-dimethyl-1-(6-(quinolin-4-yl)-4-(trifluoromethyl)pyridin-3-yl)oxy)pentan-2-amine;
(S)-methyl (5-((2-amino-2,4-dimethylpentyl)oxy)-4-(trifluoromethyl)-[2,4'-bipyridin]-2'-yl)carbamate;
(S)-1-((2'-chloro-4-(difluoromethyl)-[2,4'-bipyridin]-5-yl)oxy)-2,4-dimethylpentan-2-amine;
(S)-1-((4-(difluoromethyl)-5'-fluoro-2'-methyl-[2,4'-bipyridin]-5-yl)oxy)-2,4-dimethylpentan-2-amine;
(S)-1-((4-(difluoromethyl)-3'-fluoro-2'-methyl-[2,4'-bipyridin]-5-yl)oxy)-2,4-dimethylpentan-2-amine;
(S)-1-((4-(difluoromethyl)-6-(2-methylpyrimidin-4-yl)pyridin-3-yl)oxy)-2,4-dimethylpentan-2-amine;
(S)-1-(2-(difluoromethyl)-4-(2-methylpyrimidin-4-yl)phenoxy)-2,4-dimethylpentan-2-amine;
(S)-5-((2-amino-2,4-dimethylpentyl)oxy)-3'-fluoro-6-methyl-[2,4'-bipyridin]-2'-amine;
(S)-1-((2'-chloro-3'-fluoro-6-methyl-[2,4'-bipyridin]-5-yl)oxy)-2,4-dimethylpentan-2-amine;
(S)-methyl (5-((2-amino-2,4-dimethylpentyl)oxy)-5'-fluoro-6-methyl-[2,4'-bipyridin]-2'-yl)carbamate;

(S)-1-((2'-chloro-5'-fluoro-6-methyl-[2,4'-bipyridin]-5-yl)oxy)-2,4-dimethylpentan-2-amine;
(S)-methyl (5-((2-amino-2,4-dimethylpentyl)oxy)-3'-fluoro-6-methyl-[2,4'-bipyridin]-2'-yl)carbamate;
(S)-1-((2'-chloro-6-(difluoromethyl)-[2,4'-bipyridin]-5-yl)oxy)-2,4-dimethylpentan-2-amine;
(S)-1-((2'-chloro-6-(difluoromethyl)-3'-fluoro-[2,4'-bipyridin]-5-yl)oxy)-2,4-dimethylpentan-2-amine;
(S)-1-((6-(difluoromethyl)-3'-fluoro-2'-methyl-[2,4'-bipyridin]-5-yl)oxy)-2,4-dimethylpentan-2-amine;
((S)-1-((6-chloro-2'-(difluoromethyl)-[2,4'-bipyridin]-5-yl)oxy)-2,4-dimethylpentan-2-amine;
(S)-1-((4-(difluoromethyl)-6-(6-methylpyridazin-4-yl)pyridin-3-yl)oxy)-2,4-dimethylpentan-2-amine;
(S)-1-((2-(difluoromethyl)-6-(6-methylpyridazin-4-yl)pyridin-3-yl)oxy)-2,4-dimethylpentan-2-amine;
(R)-2,4-dimethyl-1-((2'-methyl-4-(trifluoromethyl)-[2,4'-bipyridin]-5-yl)oxy)pentan-2-amine;
(R)-2,4-dimethyl-1-((6-(quinolin-4-yl)-4-(trifluoromethyl)pyridin-3-yl)oxy)pentan-2-amine;
(R)-methyl (5-((2-amino-2,4-dimethylpentyl)oxy)-4-(trifluoromethyl)-[2,4'-bipyridin]-2'-yl)carbamate;
(R)-1-((2'-chloro-4-(difluoromethyl)-3'-fluoro-[2,4'-bipyridin]-5-yl)oxy)-2,4-dimethylpentan-2-amine;
(R)-1-((2'-chloro-4-(difluoromethyl)-5'-fluoro-[2,4'-bipyridin]-5-yl)oxy)-2,4-dimethylpentan-2-amine;
(R)-1-((2'-chloro-4-(difluoromethyl)-[2,4'-bipyridin]-5-yl)oxy)-2,4-dimethylpentan-2-amine;
(R)-1-((4-(difluoromethyl)-2'-ethyl-[2,4'-bipyridin]-5-yl)oxy)-2,4-dimethylpentan-2-amine;
(R)-1-((4-(difluoromethyl)-5'-fluoro-2'-methyl-[2,4'-bipyridin]-5-yl)oxy)-2,4-dimethylpentan-2-amine;
(R)-1-((4-(difluoromethyl)-3'-fluoro-2'-methyl-[2,4'-bipyridin]-5-yl)oxy)-2,4-dimethylpentan-2-amine;
(R)-methyl (5-((2-amino-2,4-dimethylpentyl)oxy)-6-methyl-[2,4'-bipyridin]-2'-yl)carbamate;
(R)-1-((2',6-bis(difluoromethyl)-[2,4'-bipyridin]-5-yl)oxy)-2,4-dimethylpentan-2-amine;
(R)-1-((2',4-bis(difluoromethyl)-[2,4'-bipyridin]-5-yl)oxy)-2,4-dimethylpentan-2-amine;
(S)-methyl (4-(difluoromethyl)-5-((2-hydroxy-2,4-dimethylpentyl)oxy)-[2,4'-bipyridin]-2'-yl)carbamate;
(S)-1-((4-(difluoromethyl)-2'-methyl-[2,4'-bipyridin]-5-yl)oxy)-2,4-dimethylpentan-2-ol; (S)-methyl (5-((2-amino-2-(fluoromethyl)-4-methylpentyl)oxy)-6-(difluoromethyl)-[2,4'-bipyridin]-2'-yl)carbamate;
(R)-methyl (5-((2-amino-2-(fluoromethyl)-4-methylpentyl)oxy)-6-(difluoromethyl)-[2,4'-bipyridin]-2'-yl)carbamate;
(S)-methyl (5-((2-amino-2-(fluoromethyl)-4-methylpentyl)oxy)-4-(difluoromethyl)-[2,4'-bipyridin]-2'-yl)carbamate;
(R)-methyl (5-((2-amino-2-(fluoromethyl)-4-methylpentyl)oxy)-4-(difluoromethyl)-[2,4'-bipyridin]-2'-yl)carbamate;
(S)-1-((2',6-bis(difluoromethyl)-[2,4'-bipyridin]-5-yl)oxy)-2-(fluoromethyl)-4-methylpentan-2-amine;
(S)-1-((2',4-bis(difluoromethyl)-[2,4'-bipyridin]-5-yl)oxy)-2-(fluoromethyl)-4-methylpentan-2-amine;
(R)-1-((2',6-bis(difluoromethyl)-[2,4'-bipyridin]-5-yl)oxy)-2-(fluoromethyl)-4-methylpentan-2-amine;
(R)-1-((2',4-bis(difluoromethyl)-[2,4'-bipyridin]-5-yl)oxy)-2-(fluoromethyl)-4-methylpentan-2-amine;
(S)-1-((4-(difluoromethyl)-2'-methyl-[2,4'-bipyridin]-5-yl)oxy)-2-(fluoromethyl)-4-methylpentan-2-amine;
(R)-1-((4-(difluoromethyl)-2'-methyl-[2,4'-bipyridin]-5-yl)oxy)-2-(fluoromethyl)-4-methylpentan-2-amine;
(S)—N-(4-(4-((2-amino-4-methylpentyl)oxy)-3-fluorophenyl)pyridin-2-yl)acetamide;
(S)-1-((3-chloro-5-(7-fluoroquinolin-4-yl)pyridin-2-yl)oxy)-2,4-dimethylpentan-2-amine;
(S)-1-((3-chloro-5-(6-fluoroquinolin-4-yl)pyridin-2-yl)oxy)-2,4-dimethylpentan-2-amine;
(S)-1-((3-chloro-5-(2-methylpyrimidin-4-yl)pyridin-2-yl)oxy)-2,4-dimethylpentan-2-amine;
(S)-1-((2'-chloro-5-(difluoromethyl)-[3,4'-bipyridin]-6-yl)oxy)-2,4-dimethylpentan-2-amine;
(S)-1-((5-(difluoromethyl)-2'-methyl-[3,4'-bipyridin]-6-yl)oxy)-2,4-dimethylpentan-2-amine;
(S)-1-((3-(difluoromethyl)-5-(7-fluoroquinolin-4-yl)pyridin-2-yl)oxy)-2,4-dimethylpentan-2-amine;
(S)-methyl (6-((2-amino-2,4-dimethylpentyl)oxy)-5-(difluoromethyl)-[3,4'-bipyridin]-2'-yl)carbamate;
(S)-1-((5-(7-chloroquinolin-4-yl)-3-(difluoromethyl)pyridin-2-yl)oxy)-2,4-dimethylpentan-2-amine;
(S)-1-((3-(difluoromethyl)-5-(2-methylpyrimidin-4-yl)pyridin-2-yl)oxy)-2,4-dimethylpentan-2-amine;
(S)-1-((2',5-bis(difluoromethyl)-[3,4'-bipyridin]-6-yl)oxy)-2,4-dimethylpentan-2-amine;
(S)-1-((3-(difluoromethyl)-5-(6-fluoroquinolin-4-yl)pyridin-2-yl)oxy)-2,4-dimethylpentan-2-amine;
(S)-1-((3-(difluoromethyl)-5-(5,7-difluoroquinolin-4-yl)pyridin-2-yl)oxy)-2,4-dimethylpentan-2-amine;
(S)-1-((3-(difluoromethyl)-5-(7-(trifluoromethyl)quinolin-4-yl)pyridin-2-yl)oxy)-2,4-dimethylpentan-2-amine;
(S)-1-((5-(difluoromethyl)-2',3'-dimethyl-[3,4'-bipyridin]-6-yl)oxy)-2,4-dimethylpentan-2-amine;
(S)-1-((3-(difluoromethyl)-5-(quinolin-4-yl)pyridin-2-yl)oxy)-2,4-dimethylpentan-2-amine;
(S)-1-((3-(difluoromethyl)-5-(7-methylquinolin-4-yl)pyridin-2-yl)oxy)-2,4-dimethylpentan-2-amine;
(S)-methyl (5-((2-amino-2,4-dimethylpentyl)oxy)-4-methoxy-[2,4'-bipyridin]-2'-yl)carbamate;
(S)-1-((2'-(difluoromethyl)-4-methoxy-[2,4'-bipyridin]-5-yl)oxy)-2,4-dimethylpentan-2-amine;
(S)-methyl (4-(4-((2-amino-2,4-dimethylpentyl)oxy)naphthalen-1-yl)pyridin-2-yl)carbamate;
(S)-2,4-dimethyl-1-((4-(quinolin-4-yl)naphthalen-1-yl)oxy)pentan-2-amine;
(S)-methyl (4-(5-((2-amino-2,4-dimethylpentyl)oxy)pyrimidin-2-yl)pyridin-2-yl)carbamate;
(S)-methyl (4-(2-((2-amino-2,4-dimethylpentyl)oxy)pyrimidin-5-yl)pyridin-2-yl)carbamate;
(S)-2,4-dimethyl-1-((2',4,6-trimethyl-[2,4'-bipyridin]-5-yl)oxy)pentan-2-amine;
(S)-methyl (5-((2-amino-2,4-dimethylpentyl)oxy)-4,6-dimethyl-[2,4'-bipyridin]-2'-yl)carbamate;
(S)-2,4-dimethyl-1-(4-(quinazolin-4-yl)-2-(trifluoromethyl)phenoxy)pentan-2-amine;
(S)-1-(4-(3,6-dihydro-2H-pyran-4-yl)-2-(trifluoromethyl)phenoxy)-2,4-dimethylpentan-2-amine;
(S)-2,4-dimethyl-1-(4-(2-methylquinolin-4-yl)-2-(trifluoromethyl)phenoxy)pentan-2-amine;
(S)-1-(4-(6-chloroquinolin-4-yl)-2-(trifluoromethyl)phenoxy)-2,4-dimethylpentan-2-amine;
(S)-1-((5-(5,7-difluoroquinolin-4-yl)-3-(trifluoromethyl)pyridin-2-yl)oxy)-2,4-dimethylpentan-2-amine;
(S)-2,4-dimethyl-1-((5-(quinolin-4-yl)-3-(trifluoromethyl)pyridin-2-yl)oxy)pentan-2-amine;
(S)-methyl (6-((2-amino-2,4-dimethylpentyl)oxy)-5-(trifluoromethyl)-[3,4'-bipyridin]-2'-yl)carbamate;
(S)-2,4-dimethyl-1-((2'-methyl-5-(trifluoromethyl)-[3,4'-bipyridin]-6-yl)oxy)pentan-2-amine;
(S)-1-((5-(6-chloroquinolin-4-yl)-3-methylpyridin-2-yl)oxy)-2,4-dimethylpentan-2-amine;

(S)-1-((5-(6-fluoroquinolin-4-yl)-3-methylpyridin-2-yl)oxy)-2,4-dimethylpentan-2-amine;
(S)-1-((5-(5,7-difluoroquinolin-4-yl)-3-methylpyridin-2-yl)oxy)-2,4-dimethylpentan-2-amine;
(S)-1-((5-(7-chloroquinolin-4-yl)-3-methylpyridin-2-yl)oxy)-2,4-dimethylpentan-2-amine;
(S)-1-((6-(5,7-difluoroquinolin-4-yl)-4-methylpyridin-3-yl)oxy)-2,4-dimethylpentan-2-amine;
(S)-1-((6-(7-fluoroquinolin-4-yl)-4-methylpyridin-3-yl)oxy)-2,4-dimethylpentan-2-amine;
(S)-1-((2',4-dimethyl-[2,4'-bipyridin]-5-yl)oxy)-2,4-dimethylpentan-2-amine;
(S)-1-((6-(6-chloroquinolin-4-yl)-4-methylpyridin-3-yl)oxy)-2,4-dimethylpentan-2-amine;
(S)-1-((6-(6-fluoroquinolin-4-yl)-4-methylpyridin-3-yl)oxy)-2,4-dimethylpentan-2-amine;
(S)-1-((6-(7-chloroquinolin-4-yl)-4-methylpyridin-3-yl)oxy)-2,4-dimethylpentan-2-amine;
(S)-1-((6-(7-fluoroquinolin-4-yl)-4-methylpyridin-3-yl)oxy)-2,4-dimethylpentan-2-amine;
(S)-1-((4-chloro-6-(5,7-difluoroquinolin-4-yl)pyridin-3-yl)oxy)-2,4-dimethylpentan-2-amine;
(S)-1-((4-chloro-[2,4'-bipyridin]-5-yl)oxy)-2,4-dimethylpentan-2-amine;
(S)-1-((4-chloro-6-(6-fluoroquinolin-4-yl)pyridin-3-yl)oxy)-2,4-dimethylpentan-2-amine;
(S)-1-((4-chloro-6-(quinolin-4-yl)pyridin-3-yl)oxy)-2,4-dimethylpentan-2-amine;
(S)-methyl (5-((2-amino-2,4-dimethylpentyl)oxy)-4-chloro-[2,4'-bipyridin]-2'-yl)carbamate;
(S)-1-((4-chloro-2'-methyl-[2,4'-bipyridin]-5-yl)oxy)-2,4-dimethylpentan-2-amine;
(S)-1-((4-chloro-6-(6-chloroquinolin-4-yl)pyridin-3-yl)oxy)-2,4-dimethylpentan-2-amine;
(S)-1-((2',4-dichloro-[2,4'-bipyridin]-5-yl)oxy)-2,4-dimethylpentan-2-amine;
(S)-1-((4-chloro-6-(7-fluoroquinolin-4-yl)pyridin-3-yl)oxy)-2,4-dimethylpentan-2-amine;
(S)-1-((4-chloro-6-(7-(trifluoromethyl)quinolin-4-yl)pyridin-3-yl)oxy)-2,4-dimethylpentan-2-amine;
(S)-1-((4-chloro-2',3'-dimethyl-[2,4'-bipyridin]-5-yl)oxy)-2,4-dimethylpentan-2-amine;
(S)-1-((5-(difluoromethyl)-2'-methyl-[3,4'-bipyridin]-6-yl)oxy)-2,4-dimethylpentan-2-amine;
(R)-methyl (6-((2-amino-2,4-dimethylpentyl)oxy)-5-(difluoromethyl)-[3,4'-bipyridin]-2'-yl)carbamate;
(R)-1-((3-(difluoromethyl)-5-(quinolin-4-yl)pyridin-2-yl)oxy)-2,4-dimethylpentan-2-amine;
(R)-1-((3-(difluoromethyl)-5-(2-methylpyrimidin-4-yl)pyridin-2-yl)oxy)-2,4-dimethylpentan-2-amine;
(R)-1-((3-(difluoromethyl)-5-(5,7-difluoroquinolin-4-yl)pyridin-2-yl)oxy)-2,4-dimethylpentan-2-amine;
(R)-1-((5-(7-chloroquinolin-4-yl)-3-(difluoromethyl)pyridin-2-yl)oxy)-2,4-dimethylpentan-2-amine;
N-(4'-((2-amino-2,4-dimethylpentyl)oxy)-3'-methyl-[1,1'-biphenyl]-3-yl)acetamide;
(S)-1-(4-(2-(difluoromethyl)pyridin-4-yl)-2-(trifluoromethyl)phenoxy)-2,4-dimethylpentan-2-amine;
(S)-2,4-dimethyl-1-(4-(2-methylpyridin-4-yl)-2-(trifluoromethyl)phenoxy)pentan-2-amine;
(S)-methyl (5-((2-amino-2,4-dimethylpentyl)oxy)-6-methyl-[2,4'-bipyridin]-2'-yl)carbamate;
(S)-1-((4-(difluoromethyl)-2'-methyl-[2,4'-bipyridin]-5-yl)oxy)-2,4-dimethylpentan-2-amine;
(S)-1-((2',6-bis(difluoromethyl)-[2,4'-bipyridin]-5-yl)oxy)-2,4-dimethylpentan-2-amine;

(S)-2,4-dimethyl-1-((2'-methyl-4-(trifluoromethyl)-[2,4'-bipyridin]-5-yl)oxy)pentan-2-amine;
(S)-1-((4-(difluoromethyl)-3'-fluoro-2'-methyl-[2,4'-bipyridin]-5-yl)oxy)-2,4-di methylpentan-2-amine;
(S)-1-((6-(difluoromethyl)-3'-fluoro-2'-methyl-[2,4'-bipyridin]-5-yl)oxy)-2,4-dimethylpentan-2-amine;
(S)-1-((3-(difluoromethyl)-5-(2-methylpyrimidin-4-yl)pyridin-2-yl)oxy)-2,4-dimethylpentan-2-amine;
(S)-1-((4-chloro-2'-methyl-[2,4'-bipyridin]-5-yl)oxy)-2,4-dimethylpentan-2-amine;
and pharmaceutically acceptable salts thereof.

A preferred AAK1 inhibitor is (S)-1-((2',6-bis(difluoromethyl)-[2,4'-bipyridin]-5-yl)oxy)-2,4-dimethylpentan-2-amine:

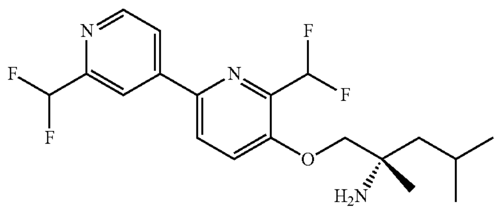 [SMILES: CC(C)C[C@](C)(N)COc1ccc(-c2ccnc(C(F)F)c2)nc1C(F)F]

(referred to herein as "Compound 1") or a pharmaceutically acceptable salt thereof. A specific salt of Compound 1 is ((S)-1-((2',6-bis(difluoromethyl)-[2,4'-bipyridin]-5-yl)oxy)-2,4-dimethylpentan-2-aminium dihydrogen phosphate.

The AAK1 inhibitors disclosed herein may exist in various solid (e.g., crystalline) forms. A particular solid form of ((S)-1-((2',6-bis(difluoromethyl)-[2,4'-bipyridin]-5-yl)oxy)-2,4-dimethylpentan-2-aminium dihydrogen phosphate, referred to herein as Form I, is described in U.S. patent application Ser. No. 18/114,104, filed Feb. 24, 2023, and U.S. provisional patent application No. 63/315,507, filed Mar. 1, 2022. Crystalline Form I has an XRPD spectrum with diffraction peaks at one or more of about 4.81, 5.99, 7.44, 7.89, 11.66, 14.85, 15.77, 19.19, 20.86, 21.65, 23.96, 24.48, or 24.73 degrees 2-theta (e.g., as measured using a Bruker X-ray diffractometer with a LYNXEYE detector (copper Kα radiation)). When used herein to refer to XPRD peaks, the term "about" means±0.2 degrees 2-theta. Crystalline Form I has a melting point of about 184° C. as determined by differential scanning calorimetry (DSC) (melting endotherm). When referring to a temperature, the terms "substantially" and "about" mean±2° C.

The AAK1 inhibitors disclosed herein can be prepared by methods known in the art. See, e.g., U.S. Pat. No. 9,902,722; Hartz, R. A., supra; Luo G., et al., J Med Chem. 2022 Mar. 24; 65(6):4534-4564; and Luo G, et al., J Med Chem. 2022 Mar. 24; 65(6):4457-4480.

Pharmaceutical Compositions Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free-flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of Formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phophatidylcholines.

The compounds of Formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain antioxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

Methods of Treatment

This invention is directed, in part, to methods of treating, managing, and preventing spasticity in a patient. Spasticity is defined as a velocity-dependent increase in tonic stretch reflexes with exaggerated movements due to the hyperexcitability of stretch reflexes.

Characteristics and qualities of spasticity include: increased tone, which is an enhanced response to muscle stretch as well as a decreased modulation of stretch reflexes; spasms, which are involuntary, repetitive, and sustained movements usually involving multiple muscle groups and joints; and clonus, which are involuntary contractions in a rhythmic pattern in response to sudden stretch of a muscle. Chang, supra. Most cases of spasticity can be subdivided into spinal or cerebral spasticity. Spinal spasticity results from the removal or destruction of supraspinal control and leads to increased excitability of motor neurons, whereas cerebral spasticity stems from a loss of descending inhibition.

Particular embodiments of the invention comprise methods of treating, managing, or preventing spasticity in a patient, which comprise inhibiting AAK1 in the patient. In preferred embodiments, the AAK1 inhibition is achieved by administering to the patient an effective amount of an AAK1 inhibitor. Preferred AAK1 inhibitors penetrate the central nervous system, and are disclosed herein. A particularly preferred AAK1 inhibitor is (S)-1-((2',6-bis(difluoromethyl)-[2,4'-bipyridin]-5-yl)oxy)-2,4-dimethylpentan-2-amine or a pharmaceutically acceptable salt thereof.

Particular embodiments of the invention comprise methods of preventing spasticity in a patient in need thereof, which comprise administering a prophylactically effective amount of an AAK1 inhibitor to the patient. Patients in need of such prevention include those suffering from spinal cord injury (SCI), cerebral palsy, stroke, amyotrophic lateral sclerosis, or multiple sclerosis (MS).

Particular embodiments of the invention comprise methods of treating spasticity in a patient in need thereof, which comprise administering a therapeutic effective amount of an AAK1 inhibitor to the patient. Patients in need of such treatment include those suffering from SCI, cerebral palsy, stroke, amyotrophic lateral sclerosis, or MS.

In certain embodiments, the AAK1 inhibitor is administered in combination—albeit not necessarily at the same time or in the same pharmaceutical formulation—with another therapeutic commonly used to treat spasticity. Examples of such therapeutics include centrally acting agents such as baclofen, clonidine, and tizanidine, anticonvulsants such as benzodiazepines and gabapentin, and peripherally acting agents such as dantrolene.

An AAK1 inhibitor may be administered to a subject in one or more doses. In some embodiments, the AAK1 inhibitor is administered in an amount of about 10 mg to 1000 mg per dose, e.g., about 10 mg to 20 mg, about 20 mg to 25 mg, about 25 mg to 50 mg, about 50 mg to 75 mg, about 75 mg to 100 mg, about 100 mg to 125 mg, about 125 mg to 150 mg, about 150 mg to 175 mg, about 175 mg to 200 mg, about 200 mg to 225 mg, about 225 mg to 250 mg, about 250 mg to 300 mg, about 300 mg to 350 mg, about 350 mg to 400 mg, about 400 mg to 450 mg, about 450 mg to 500 mg, about 500 mg to 750 mg, or about 750 mg to 1000 mg per dose. In some embodiments, the AAK1 inhibitor is administered to the subject in one or more single dose(s) of about 40 mg. In some embodiments, the AAK1 inhibitor is administered to the subject in one or more single dose(s) of about 200 mg.

In some embodiments, the amount of the AAK1 inhibitor per dose is determined on a per body weight basis. For example, in some embodiments, the AAK1 inhibitor is administered in an amount of about 0.5 mg/kg to 100 mg/kg, e.g., about 0.5 mg/kg to 1 mg/kg, about 1 mg/kg to 2 mg/kg, about 2 mg/kg to 3 mg/kg, about 3 mg/kg to 5 mg/kg, about 5 mg/kg to 7 mg/kg, about 7 mg/kg to about 10 mg/kg, about 10 mg/kg to 15 mg/kg, about 15 mg/kg to 20 mg/kg, about 20 mg/kg to 25 mg/kg, about 25 mg/kg to 30 mg/kg, about 30 mg/kg to 40 mg/kg, about 40 mg/kg to 50 mg/kg, about 50 mg/kg to 60 mg/kg, about 60 mg/kg to 70 mg/kg, about 70 mg/kg to 80 mg/kg, about 80 mg/kg to 90 mg/kg, or about 90 mg/kg to 100 mg/kg, or more than about 100 mg/kg.

Those of skill will readily appreciate that dose levels can vary as a function of several different factors including, without limitation, the specific AAK1 inhibitor administered, the severity of the symptoms, the age and/or physical size of the subject, and the susceptibility of the subject to side effects. Preferred dosages for a given compound are readily determinable by those of skill in the art by a variety of means.

In some embodiments, multiple doses of the AAK1 inhibitor are administered. The frequency of administration of the AAK1 inhibitor can vary depending on any of a variety of factors, e.g., severity of the symptoms, and the like. For example, in some embodiments, the AAK1 inhibitor is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). As discussed above, in some embodiments, the AAK1 inhibitor is administered continuously.

The duration of administration may vary depending on any of a variety of factors known by those skilled in the art (e.g., patient response, route of administration, dosage form). For example, the AAK1 inhibitor may be administered over a period of time of about one day to one week, about two weeks to four weeks, about one month to two months, about two months to four months, about four months to six months, about six months to eight months, about eight months to 1 year, about 1 year to 2 years, or more.

Embodiments of the present invention provide methods and compositions for the administration of the AAK1 inhibitor to a patient (e.g., a human) using any available method and route suitable for drug delivery, including in vivo and ex vivo methods, as well as systemic and localized routes of administration.

Routes of administration include oral, intranasal, intramuscular, intratracheal, subcutaneous, intradermal, topical application, intravenous, rectal, nasal, and other enteral and parenteral routes of administration. Routes of administration may be combined, if desired, or adjusted depending upon the agent and/or the desired effect. An active agent may be administered in a single dose or in multiple doses using conventional methods and routes suitable for delivery of conventional drugs, including systemic or localized routes.

In general, routes of administration contemplated by the disclosure include, but are not limited to, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes. Parenteral administration can be conducted to effect systemic or local delivery of the AAK1 inhibitor. Where systemic delivery is desired, administration typically involves invasive or systemically absorbed topical or mucosal administration of pharmaceutical preparations.

The AAK1 inhibitor may also be delivered to the subject by enteral administration. Enteral routes of administration include, but are not limited to, oral and rectal delivery.

Methods of administration through the skin or mucosa include, but are not limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available patches that deliver their product continuously via electric pulses through unbroken skin for periods of several days or more.

In some embodiments, the pharmaceutical composition is administered orally, intravenously, subcutaneously, epidurally, intraventricularly, intramuscularly, intraperitoneally, or via inhalation. In some embodiments, the pharmaceutical composition is administered orally.

A preferred method of administering Compound 1 is oral, once daily, at a dose of from about 3 mg/kg to 30 mg/kg. In one method, Compound 1 is first administered to a human patient with a 100 mg loading dose, followed by 10 mg maintenance doses thereafter. In another, Compound 1 is first administered to a human patient with a 200 mg loading dose, followed by 20 mg maintenance doses thereafter.

EXAMPLES

Aspects of particular embodiments of this invention are illuminated by the following examples.

Tablet Dosage Forms

Tablets comprising 10, 20, or 50 mg of Compound 1 as a dihydrogen phosphate salt were prepared in a batch of 20,000 using the ingredients shown below:

TABLE 1

| | Amount (mg) Per | | |
|---|---|---|---|
| Ingredient | 10 mg batch | 20 mg batch | 50 mg batch |
| Compound 1[1,2] | 252.8 | 505.6 | 1264.0 |
| Silicified Microcrystalline Cellulose | 2758.6 | 2632.2 | 2253.0 |
| Dibasic Calcium Phosphate, Anhydrous | 2758.6 | 2632.2 | 2253.0 |
| Croscarmellose Sodium | 120.0 | 120.0 | 120.0 |
| Talc | 120.0 | 120.0 | 120.0 |

TABLE 1-continued

| | Amount (mg) Per | | |
|---|---|---|---|
| Ingredient | 10 mg batch | 20 mg batch | 50 mg batch |
| Colloidal Silicon Dioxide | 30.0 | 30.0 | 30.0 |
| Hydrogenated Vegetable Oil | 160.0 | 160.0 | 160.0 |
| Total (Core Tablet) | 6200.0 | 6200.0 | 6200.0 |
| OpaDry II White[3] | 248.0 | 248.0 | 248.0 |
| Total (Film coated Tablet) | 6448.0 | 6448.0 | 6448.0 |

[1]One mg of Compound 1 is equivalent to 0.7973 mg of the corresponding free base.
[2]The quantity of Compound 1 is adjusted for potency based on the supplier Certificate of Analysis, Assay (Weight %, HPLC). A proportionate quantity of Silicified Microcrystalline Cellulose and Dibasic Calcium Phosphate, Anhydrous is adjusted accordingly.
[3]Opadry II White is dispersed in Purified Water at 15% solids to coat the cores. A 50% overage of the coating is prepared to compensate for losses during film-coating and to guarantee the amount applied per tablet. Purified Water is removed during production.

The following steps were followed to prepare solid oral dosage forms of Compound 1:

1. The quantity of Compound 1 is adjusted for potency based on the supplier Certificate of Analysis, Assay (Weight %, HPLC).
2. Screen Compound 1, Silicified Microcrystalline Cellulose, Dibasic Calcium Phosphate, Anhydrous, Croscarmellose Sodium into a bin blender and blend. Note: A proportionate quantity of Silicified Microcrystalline Cellulose and Dibasic Calcium Phosphate, Anhydrous is adjusted according to the Compound 1 potency, as determined in Step 1.
3. Screen Talc and Colloidal Silicon Dioxide into the blend from Step 2 and blend.
4. Screen Hydrogenated Vegetable Oil into the blend from Step 3 and blend.
5. Compress the blend from Step 4.
6. The tablet cores, from Step 5, are subsequently coated with an aqueous dispersion of Opadry II White for an approximate weight gain of 4%.
7. The coated tablets, from Step 6, are packaged into HDPE bottles induction sealed with a child resistant cap.

Experimental Autoimmune Encephalomyelitis (EAE) Model

The effect of Compound 1 on spasticity was evaluated in a myelin oligodendrocyte glycoprotein (MOG)-induced murine model of experimental autoimmune encephalomyelitis (EAE), a central nervous system (CNS) autoimmune demyelinating disease that mimics many of the clinical and pathologic features of multiple sclerosis. Gilgun-Sherki Y., et al., Neurosciences Research 47:201-207, 2003.

Preparation of Test Items. Test items were prepared following the instructions described below.

Preparation of Vehicle: 0.5% (w/w) (Hydroxypropyl)methylcellulose and 0.1% (w/w) Tween®80 in water; pH 3.0±0.2, at a dose volume of 5 ml/kg (Group 1): 1) Weigh 0.5 g of (Hydroxypropyl) methyl cellulose; 2) Add 100 μL of Tween®80; 3); Add DDW to achieve 90 mL solution; 4) Stir well to obtain a clear solution; 5) Adjust PH to 3.0±0.2 with phosphoric acid; 6) Add DDW to achieve 100 mL solution; and 7) Store at 4° C. A mouse weighing ~20 g will be dosed via PO with 0.1 mL of the Vehicle. Vehicle should be prepared once a week and stored at 4° C. The vehicle should be brought to room temperature prior to formulation of Compound 1.

Preparation of FTY720: at a dose level of 3 mg/kg, at a concentration of 0.6 mg/ml, and at a dose volume of 5 ml/kg (Group 2): 1) Take 25 mg of Fingolimod (FTY720) and dissolve in 41.7 ml of distilled water to obtain a concentration of 0.6 mg/ml; 2) Divide into aliquots of 1.8 ml and store at −20° C.; 3) Before each dosing, thaw an aliquot of the working solution. Note: Animal weighing ~20 g will be administered PO with 0.1 ml; QD.

Preparation of Compound 1 (10 mg/kg): at a dose level of 12.55 mg/kg of the salt form (which contains 79.7% of the free base) at a concentration of 2 mg/ml free base (2.51 mg/ml), and at a dose volume of 5 ml/kg (Group 3): 1) Weigh 5 mg of Compound 1; 2) Dissolve in 2 mL of Vehicle; 3) Stir and sonicate to achieve an even suspension; 4) Solution will be used within 24 hours of preparation. Note: A mouse weighing 20 g will be dosed via PO with 0.1 mL of Compound 1.

Preparation of Compound 1 (3 mg/kg): at a dose level of 3.76 mg/kg of the salt form at a concentration of 0.6 mg/ml free base (0.752 mg/ml), and at a dose volume of 5 ml/kg (Group 4): 1) Take 0.6 ml of Compound 1 solution at a concentration of 2.51 mg/ml; 2) Add 1.4 ml of the vehicle to obtain a concentration of 0.752 mg/ml; 3) Stir well. Note: A mouse weighing ~20 g will be dosed via PO with 0.1 mL of Compound 1.

Preparation of Tizanidine: at a dose level of 1 mg/kg, at a concentration of 0.2 mg/ml, and at a dose volume of 5 ml/kg (Groups 5): 1) Weigh 6 mg of Tizanidine; 2) Dissolve in 30 mL of Saline. 3) Stir well until fully dissolved. Note: Animal weighing ~20 g will be administered IP with 0.1 ml of Tizanidine.

MOG (Antigenic Item): The MOG solution is freshly prepared prior to the inoculation session by dissolving the RP-HPLC-purified lyophilized powder in phosphate buffered saline (PBS) to achieve a solution at a final injected concentration of 2 mg/ml (25 mg dissolve in 12.5 nil PBS). This concentration is appropriate for the selected dose and dose volume of 200 µg MOG in 100 µl PBS.

CFA (Sensitizing Item): Complete Freund's adjuvant (CFA) suspension containing heat-killed *Mycobacterium tuberculosis* H37 Ra at a concentration of 3 mg/mil is used as supplied.

MOG/CFA Emulsion (Antigenic/Sensitizing Items): Prior to the inoculation carried out on Study Day 0, the same volume of MOG and CFA is mixed, for example: 100 µl of MOG solution (200 µg) is emulsified with 100 µl of CFA suspension (300 µg heat-killed *Mycobacterium tuberculosis* H37 Ra). The solution is thoroughly mixed by employing two syringes connected by a Luer fitting until reaching a stable emulsion. A total dose volume of 200 µl is administered SC to each animal.

Pertussis Toxin (Immunostimulant Item): Prior to the immunostimulation injection performed on Study Day 0, the pertussis toxin (PT) stock solution is freshly prepared by dissolving the commercial PT sample with 500 µL distilled water (vial contains 50 µg) in sterile (water for injection) to achieve a stock concentration of 100 µg/ml. Prior to each injection on Study Days 0 and 2, the PT stock solution (100 µg/ml) is diluted in phosphate buffered saline (PBS) to achieve a final injected concentration of 2 µg/ml (dilution× 50), which is appropriate for the selected dose level and volume dosage. Take 0.5 ml of PT at a concentration of 100 µg/ml and dilute with 24.5 ml of PBS to achieve a solution at a concentration of 2 µg/ml in a total volume of 25 ml. Each mouse will be injected 0.15 nil IP (approximately 300 ng/mouse). Following each PT injection, the daily vial is discarded. Diluted stock solution (100 µg/ml) is kept refrigerated at 2-8° C. and is reused for the second PT injection on Study Day 2, however the solution will not be used if more than 48 hours have passed following its preparation. Thorough vortexing is required just prior to each PT injection session.

Phosphate Buffered Saline (Adjunct Item): PBS serves as a MOG and PT-diluent and is used as provided.

Water for Injection (Adjunct Item): Water for injection (DW) serves as a PT-diluent (stock concentration of 100 µg/ml) and is used as provided.

Study Design and Results. This study used sixty female young adult (10-11 weeks at study initiation) C57BL/6J mice sourced from Envigo RMS (Israel), Ltd. The animals were divided into five experimental groups:

| Group # | Group Size | Test Material | Admin. Route | Dose (mg/kg) |
|---|---|---|---|---|
| 1 | 12 | Vehicle | PO | 0 |
| 2 | 12 | Fingolimod (FTY720) | PO | 3 |
| 3 | 12 | Compound 1 | PO | 10 |
| 4 | 12 | Compound 1 | PO | 3 |
| 5 | 12 | Tizanidine | IP | 1 |

Each group received a dose volume of 5 ml/kg, and the regimen was performed daily from day 0 to 22 of the study, QD. On study day 21, half of the animals in each group was treated and tested for electrophysiology and electromyography (EMG) two hours post dosing. On study day 22, the same was performed with the remaining half of the animals in each group.

FIG. 1 provides a representation of the study. Following baseline measurements, the MOG murine model begins with a sensitization period induced by the single subcutaneous (SC) injection of MOG emulsified in Complete Freund's adjuvant (CFA) on Study Day 0, followed by intraperitoneal (IP) supplemental immunostimulation with pertussis toxin (PT) carried out once at the day of EAE induction (study day 0) and once again 48 hours later (on study day 2). As shown in FIG. 1, body weight (BW) and EAE clinical score were monitored at Baseline and then daily from Day 8 to Day 21. Mechanical allodynia was tested using the Von Frey test at Baseline and on Day 9 at various timepoints. For evaluation of spasticity, transcranial motor-evoked potentials (tcMEPs) were tested at Baseline and on Days 9 and 21-22 (half of the animals on each day). All animals were administered treatment once daily, starting on Day 0 until Day 22. Animals in Group 1 received oral (PO) treatment with the vehicle. Animals in Group 2 were treated with Fingolimod (FTY720; positive control) at a dose level of 3 mg/kg. PO. Animals in Groups 3 and 4 were treated with the test item Compound 1 at a dose level of 10 mg/kg or 3 mg/kg, PO, respectively. Animals in Group 5 were treated with Tizanidine at a dose level of 1 mg/kg, IP.

Body Weight Measurements: Animals in Group 1, treated with the vehicle, showed a gradual reduction in BW throughout the study compared to the Baseline level.

Animals treated with FTY720 at 3 mg/kg (Group 2) showed a statistically significantly higher mean BW on Days 11 to 17 compared to the vehicle treated mice (Group 1) presented as percentage from Baseline: 99.34±3.60% versus 82.06±2.35% for the vehicle, on Day 16; $p<0.0001$, using one-way ANOVA followed by Dunnett's post-hoc test.

Treatment with Tizanidine at 1 mg/kg (Group 5) resulted in higher mean BW compared to the vehicle treated group, however it was found to be statistically significant only on Day 16: 91.31±1.59% versus 82.06±2.35% for the vehicle; $p<0.05$, using one-way ANOVA followed by Dunnett's post-hoc test.

The BW of the animals following treatment with Compound 1 at 10 mg/kg or 3 mg/kg (Groups 3 and 4, respectively) was not significantly different from the vehicle group throughout the study.

EAE Clinical Score and AUC: Animals in Group 1, treated with the vehicle, showed a gradual elevation in the clinical score throughout the study, reaching a maximal score of 3.91±0.28 points on Day 17.

Animals treated with FTY720 at 3 mg/kg (Group 2), showed a statistically significantly lower clinical score on Days 11-21 compared to the vehicle-treated animals (Group 1), reaching a maximal score of 2.18±0.50 points on Days 20 and 21: 1.2710.43 points versus 3.45±0.25 points for the vehicle: $p<0.0001$ using one-way ANOVA followed by Dunnett's post-hoc test.

The difference between FTY720-treated animals (Group 2) and the vehicle-treated animals (Group 1) was also shown using the calculation of the area under the curve (AUC) of the clinical score: 12.45±3.18 points versus 29.96±3.41 for the vehicle; $p<0.001$ using one-way ANOVA followed by Dunnett's post-hoc test.

Treatment with either Compound 1 or Tizanidine did not result in a significant reduction in the clinical score compared to the vehicle.

Mechanical Allodynia Evaluation (Von Frey Testing): Animals were tested for mechanical allodynia using the Von Frey test at Baseline, and then on Day 9 at 0.5 hours (Group only), 1.5 hours, 3.5 hours (all groups) and 5.5 hours (Groups 1-4 only) post-dose.

Figure 2:
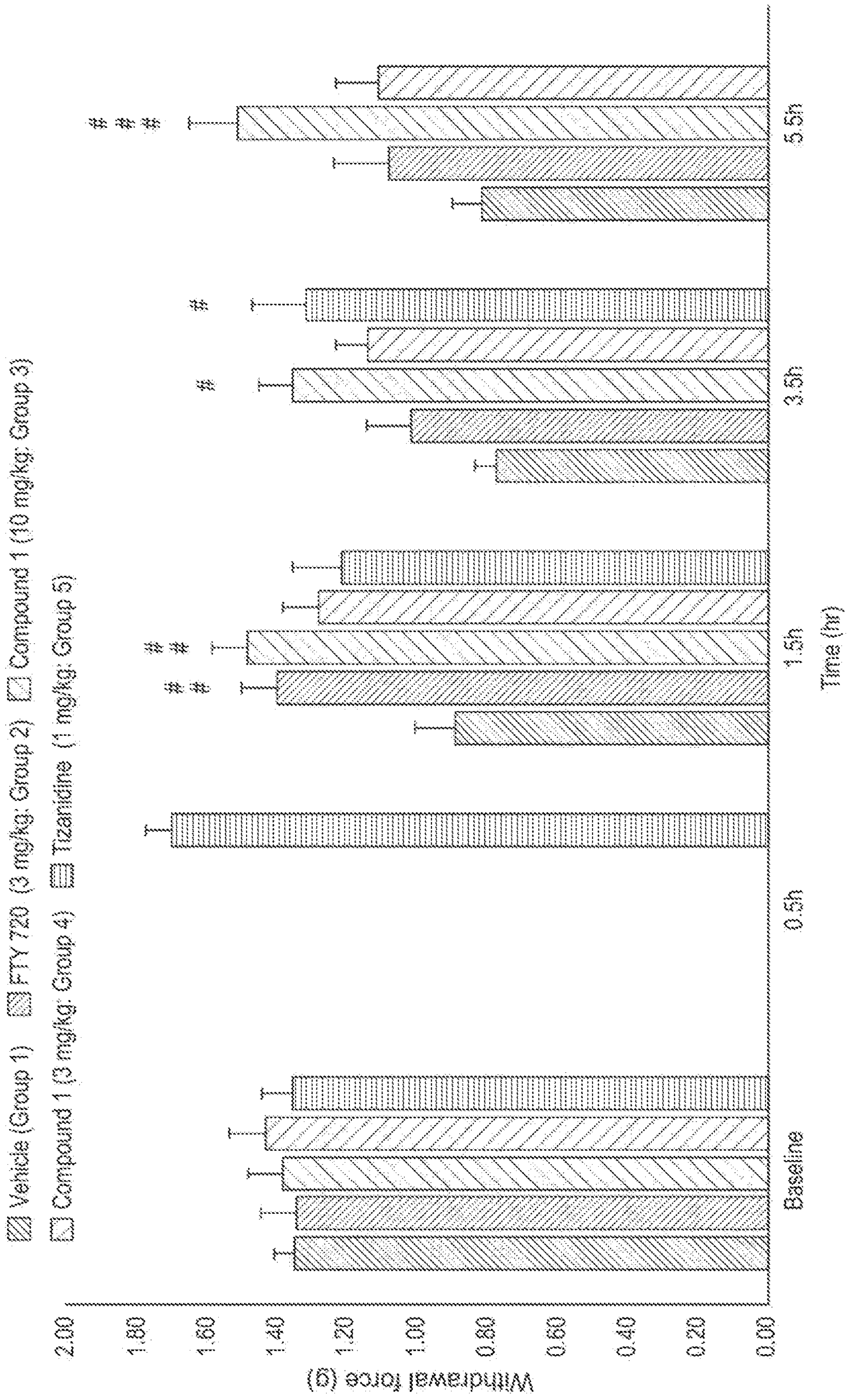
FIG. 2 shows Von Frey (VF) results post administration on Day 9 of study, where: #p<0.05 versus Vehicle (Group 1) using one-way ANOVA followed by Dunnett's test; ##p<0.01 versus Vehicle using one-way ANOVA followed by Dunnett's test; ###p<0.001 versus Vehicle using one-way ANOVA followed by Dunnett's test.

As shown in FIG. 2, animals treated with the vehicle (Group 1) exhibited a significantly lower withdrawal force threshold compared Baseline level at all time-points. Animals treated with FTY720 at 3 mg/kg (Group 2) showed a statistically significantly higher withdrawal force threshold compared to the vehicle-treated Group 1.5 hours post dosing: 1.40±0.10 g versus 0.89±0.11 g for the vehicle; $p<0.01$ using one-way ANOVA followed by Dunnett's post-hoc test. The effect was not significant at the 3.5- and 5.5-hour post-dose timepoints.

Treatment with Compound 1 at the high dose, 10 mg/kg (Group 3), resulted in a statistically significantly higher withdrawal force threshold compared to the vehicle-treated group at all timepoints (1.5, 3.5, and 5.5 hours) post dose: 1.48±0.10 g versus 0.89±0.11 g for the vehicle at 1.5 hours, 1.36±0.09 g versus 0.78±0.06 g for the vehicle at 3.5 hours, and 1.52±0.13 g versus 0.82±0.08 g for vehicle at 5.5 hours post dosing, $p<0.01$, $p<0.5$, $p<0.001$ (respectively) using one-way ANOVA followed by Dunnett's post-hoc test.

Treatment with the lower dose of Compound 1 (3 mg/kg: Group 4) also resulted in a higher withdrawal force threshold compared to the vehicle-treated group at all timepoints post dosing.

Treatment with Tizanidine at 1 mg/kg (Group 5) resulted in higher withdrawal force threshold at all timepoints (0.5, 1.5, and 3.5 hours) post-dose. However, it was found to be statistically significant compared to the vehicle group only at 3.5 hours post dosing: 1.32±0.15 g versus 0.78±0.06 g for the vehicle; $p<0.05$ using one-way ANOVA followed by Dunnett's post-hoc test.

Electrophysiology: The animals were subjected to electrophysiology testing at Baseline and Days 10 and 21 of the study. The EMG, latency, latency to main event, duration, peak-to-peak (P2P) amplitude, and number of subpeaks were recorded.

Figure 3:
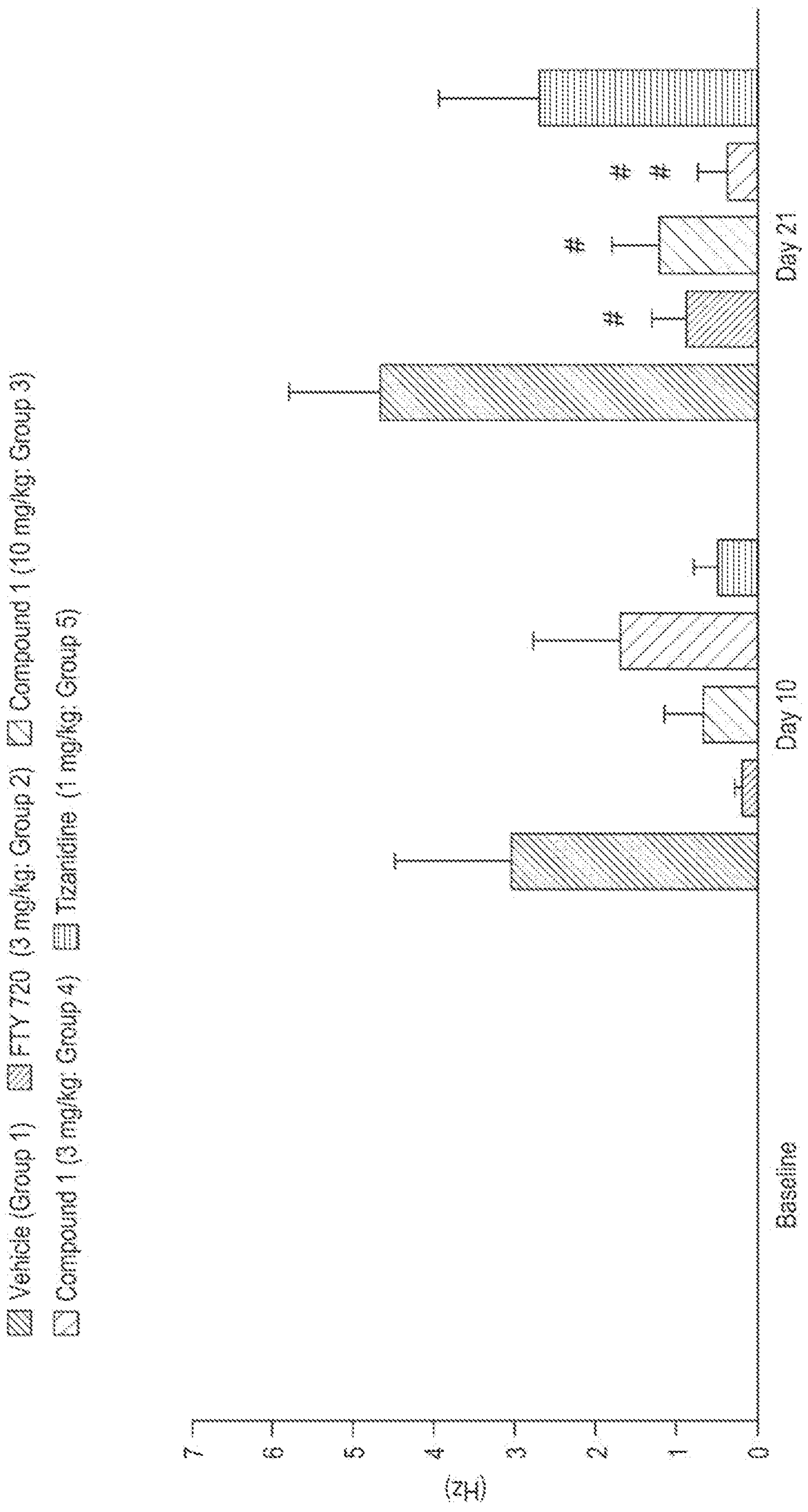
FIG. 3 shows the results of electromyographic (EMG) measurements, where: #p<0.05 versus Vehicle (Group 1) using one-way ANOVA followed by Dunnett's test; and ##p<0.01 versus Vehicle using one-way ANOVA followed by Dunnett's test.

As shown in FIG. 3, animals treated with FTY720 at 3 mg/kg (Group 2) or with Compound 1 at both doses (Groups 3 and 4) had statistically significantly lower rate of fibrillation on Day 21 compared to the vehicle: 0.41±0.89 Hz for Group 2, 1.22±0.57 Hz for Group 3, and 0.38±0.38 Hz for Group 4 versus 1.11±4.69 Hz for the vehicle-treated animals, $p<0.05$ or $p<0.01$ using one-way ANOVA followed by Dunnett's post-hoc test.

Animals treated with FTY720 at 3 mg/kg (Group 2) or with Compound 1 at both doses (Groups 3 and 4) had statistically significantly shorter latency on Day 10 compared to vehicle: 5.16±0.16 ms (Group 2), 5.54±0.22 ms (Group 3), 5.31±0.21 ms (Group 4) versus 6.94±0.59 ms of Vehicle (Group 1), $p<0.01$ and $p<0.05$ (respectively) using one-way ANOVA followed by Dunnett's post-hoc test.

Figure 4:
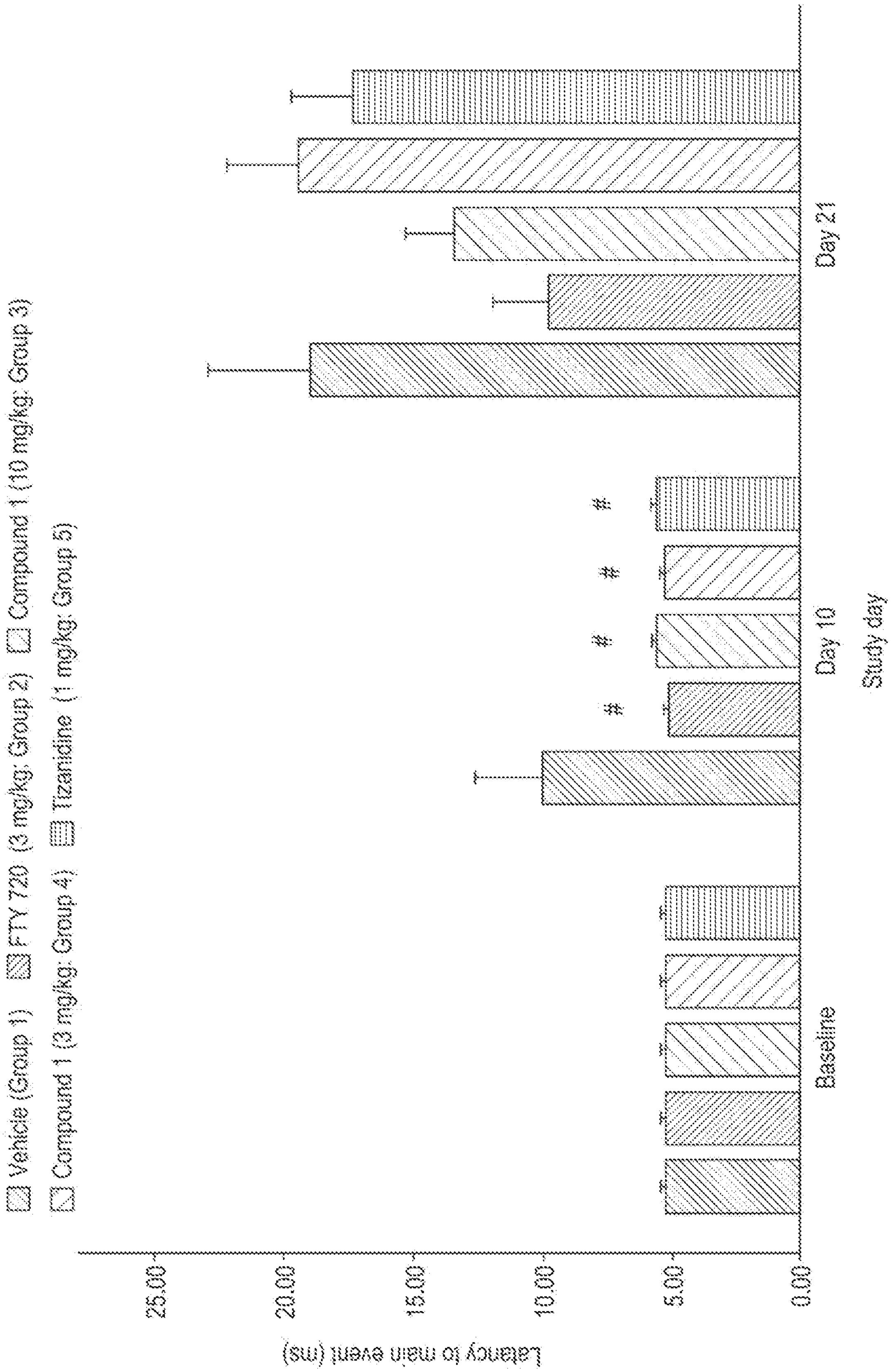
FIG. 4 shows the results of latency to main events measurements, where: #p<0.05 versus Vehicle (Group 1) using one-way ANOVA followed by Dunnett's test.

As shown in FIG. 4, animals in all test groups showed statistically significant lower latency (in milliseconds) until reaching the main event compared to the vehicle group on Day 10: 5.16±0.16 ms for FTY720; 5.5510.22 ms for Compound 1 at 10 mg/kg; 5.32±0.22 ms for Compound 1 at 3 mg/kg; 5.64±0.19 ms for Tizanidine versus 10.05±2.59 ms for the vehicle, $p<0.05$ using one-way ANOVA followed by Dunnett's post-hoc test. The duration of the signal was increased in all groups, compared to the Baseline level. No significant difference was found between groups.

Figure 5:
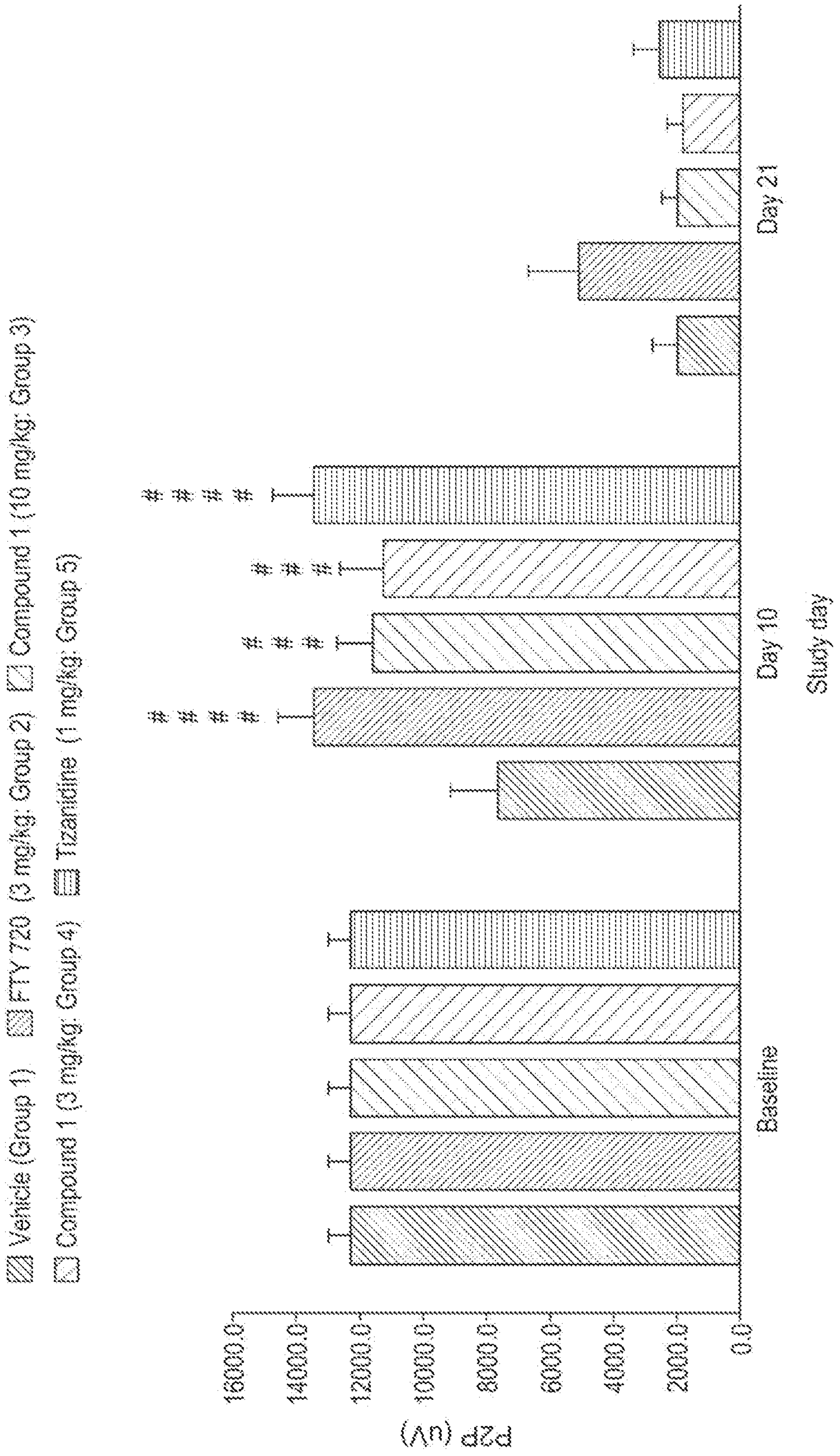
FIG. 5 shows results of peak-to-peak (P2P) amplitude measurements, where: ###p<0.001 vs. Vehicle (Group 1) using one-way ANOVA followed by Dunnett's test; and ####p<0.0001 vs. Vehicle (Group 1) using one-way ANOVA followed by Dunnett's test.

As shown in FIG. 5, the P2P amplitude measured in animals treated with vehicle gradually decreased throughout the study compared to the Baseline level. Treatment with all test items resulted in a statistically significantly higher P2P amplitude compared to the vehicle on Day 10, followed by a reduction on Day 21: FTY720 was 13472.18±1099.82 μV; Compound 1 at 10 mg/kg was 11613.75±1154.41 μV; Compound 1 at 3 mg/kg was 11321.67±1321.68 μV; and Tizanidine was 13488.71±1234.10 μV versus 7681.17±1505.12 μV for the vehicle; $p<0.05$ using one-way ANOVA followed by Dunnett's post-hoc test.

A gradual increase in the number of sub peaks was seen in all groups throughout the study. Treatment with all test items resulted in lower number of sub peaks compared to the vehicle group on Days 10 and 21. However, only treatment with FTY720 resulted in a statistically significant lower number of sub peaks on Day 21 compared to the vehicle: 1.61±0.51 versus 4.93±1.72 for the vehicle, $p<0.05$ using one-way ANOVA followed by Dunnett's post-hoc test.

Under the conditions of this study and confined to the in-life data, treatment with Compound 1 at 10 mg/kg administered once daily was effective in significantly reducing the sensitivity of the animals to mechanical stimulation. Compound 1 at 3 mg/kg, administered once daily, reduced the sensitivity of the animals to mechanical stimulation. In addition, treatment with both dose levels of Compound 1 was effective in significantly reducing the rate of fibrillation, measured using EMG, and was effective in significantly reducing latency, latency to the main event, and increasing P2P amplitude when the transcranial evoked potentials were measured. Compound 1 at both dose levels also reduced the duration and number of sub potentials when compared to vehicle treated animals.

Spinal Cord Injury

The efficacy of Compound 1 was measured in a rat model of spasticity induced by complete spinal cord transection. To induce muscle spasticity, a model of complete spinal cord transection cord at the eighth thoracic (T8) vertebral level was used. Five weeks after the Spinal Cord Injury (SCI), the rats were orally (P.O.) treated with Compound 1 (3, 10, or 30 mg/kg), Baclofen (4.5 mg/kg). Tizanidine (3 mg/kg) or vehicles alone (0.9% NaCl, Compound 1 vehicle), and the degree of spasticity response was measured using the rate-dependent depression (RDD) of the Hoffmann's reflex (H-reflex) and spasms induction.

Materials and Methods. One hundred and sixty-five rats were submitted to a complete transection of the spinal cord at the T8 vertebral level: one died during the surgical procedure; two died during the post-operative recovery period; and 1 exhibited a self-mutilation behavior and was euthanized. One hundred and fifty-one SCI rats were maintained up to the end of the 5th post-injury week. One hundred and forty rats were submitted to P.O. administration of the test compounds and EMG analysis.

One hour after the surgery, the rat was awakened with intramuscular (I.M.) injection of atipamezole (1 mg/kg; Antisedan, Orion Pharma, Espoo, Finland) and received subcutaneously 5 ml of warm NaCl (0.9%, 37° C.). It was kept in a warm chamber (38° C.) until awakening and for at least 2 additional hours. Immediately after waking, and every 8 hours for 48 hours, buprenorphine (0.05 mg/kg; Vetergesic, Sogeval, Laval, France) was subcutaneously (S.C.) administered. During the following days, its bladder was manually emptied (twice a day) until recovery of urinary function, temperature and hydration were checked and we observed any clinical sign of pain or infection.

The rat was firmly restrained to immobilize the head. In an upright position, the gavage needle was passed along the side of the mouth. Following the roof of the mouth, the needle was advanced into the esophagus and toward the stomach. After the needle is passed to the correct length, the compound was slowly injected. The rats were randomly assigned to one of the test groups:

| | |
|---|---|
| Vehicle 1 | 0.9% NaCl |
| Vehicle 2 (Compound 1 Vehicle) | 10 g of ethanol, 40 g of PEG 400, 15 g of Tween 80 |
| Compound 1 | 3 mg/kg |
| | 10 mg/kg |
| | 30 mg/kg |
| Baclofen | 4.5 mg/kg |
| Tizanidine | 3 mg/kg |

Electroneuromyographical recordings were performed in the right hind limbs before and 1, 2, 3, 4, 5 and 6 hours after P.O. administration.

Thermoregulation: Rat thorax and hind limbs were secured on a heating pad with adhesive tape. Since temperature can influence neuromuscular transmission and propagation of the action potential along the muscle fibers, body temperature was maintained at 37.5±0.5° C.

Implantation of the electrodes: For electrical stimulation and recording, four monopolar 29-gauge (12 mm length) subdermal Teflon needle electrodes (AD Instruments, Paris, France) were used. A grounding electrode was placed under the skin at the base of the tail.

Electromyographical (EMG) signals were amplified (100×) and bandpass filtered (300 Hz to 5 kHz; A-M Systems Amplifier. Everett, Washington; model 1700) before sampling at 13.5 kHz (Digidata 1440A, Molecular Devices). The tibial nerve was stimulated by using square pulses with increasing stimulus intensities (0.2 mA increments starting from 0.2 mA, 0.2 Hz, 0.2 ms; A-M systems stimulator, Model 2100) to obtain recruitment curves.

RDD of the H-reflex: To induce sedation, intraperitoneal injection of ketamine (100 mg/kg; Imalgen®) was used to suppress voluntary movements and increase muscle tone. Rats thorax and hindlimbs were secured on a heating pad with adhesive tape. The following series of measurements were repeated throughout the experiment:

1. Hmax and Mmax determination: the tibial nerve was stimulated for 0.2 ms at 0.2 Hz with increasing current intensities (1-6 mA in 0.1 mA increments) until Mmax was stabilized.
2. RDD measurement: the intensity necessary to obtain a maximal H-reflex was used for trains of 13 stimulations at 0.2, 1, 2 and 5 Hz with 2 min intervals between each train of stimulations. A whole series of measurements lasted about 15 minutes.
3. Determination of the level of RDD: at the different frequencies, responses to the first three stimulations necessary for the depression to occur were discarded, and all the responses were expressed as percentages relative to the mean response at 0.2 Hz in the same series of measurements.

Muscles spasms: In awake chronic SCI rats, muscle spasms were evoked with stimulation of the tibial nerve while performing electromyographic (EMG) recordings from the flexor digitorum brevis (FDB) muscle. Spastic spinal rats were handled nine days before the experiment and progressively habituated to be individually constrained in a plexiglass tube and to immobilization of their paralyzed hindlimbs with tape.

1. Hmax and Mmax determination: the tibial nerve was stimulated for 0.2 ms at 0.2 Hz with increasing current intensities (1-6 mA in 0.2 mA increments) until Mmax was stabilized.
2. A supramaximal single-pulse stimulation to elicit muscle spasms was fixed throughout the experiment (2 or 3 times the threshold intensity for M-wave) and evoked 5 times, with 60 s interstimulus intervals. EMG were rectified and averaged over 2000 ms interval post-stimulus to quantify spasms (Clamplit 8.0, Axon Instruments).

Data analysis: H-reflex RDDs and areas under the curves (AUC) were determined as a measurement of spasticity and analyzed at each time point and for each frequency with Mann-Whitney test or with Kruskal Wallis one-way analysis of variance (ANOVA) test, followed by Dunn's multiple comparisons test. $P<0.05$ was considered significant. Significant differences were marked with asterisks (*) according to their respective P-values: values were expressed as the mean value±standard error of the mean (SEM) in all graphs. All statistical analyses were performed using GraphPad Prism 7 (San Diego, California, USA).

Figure 6:
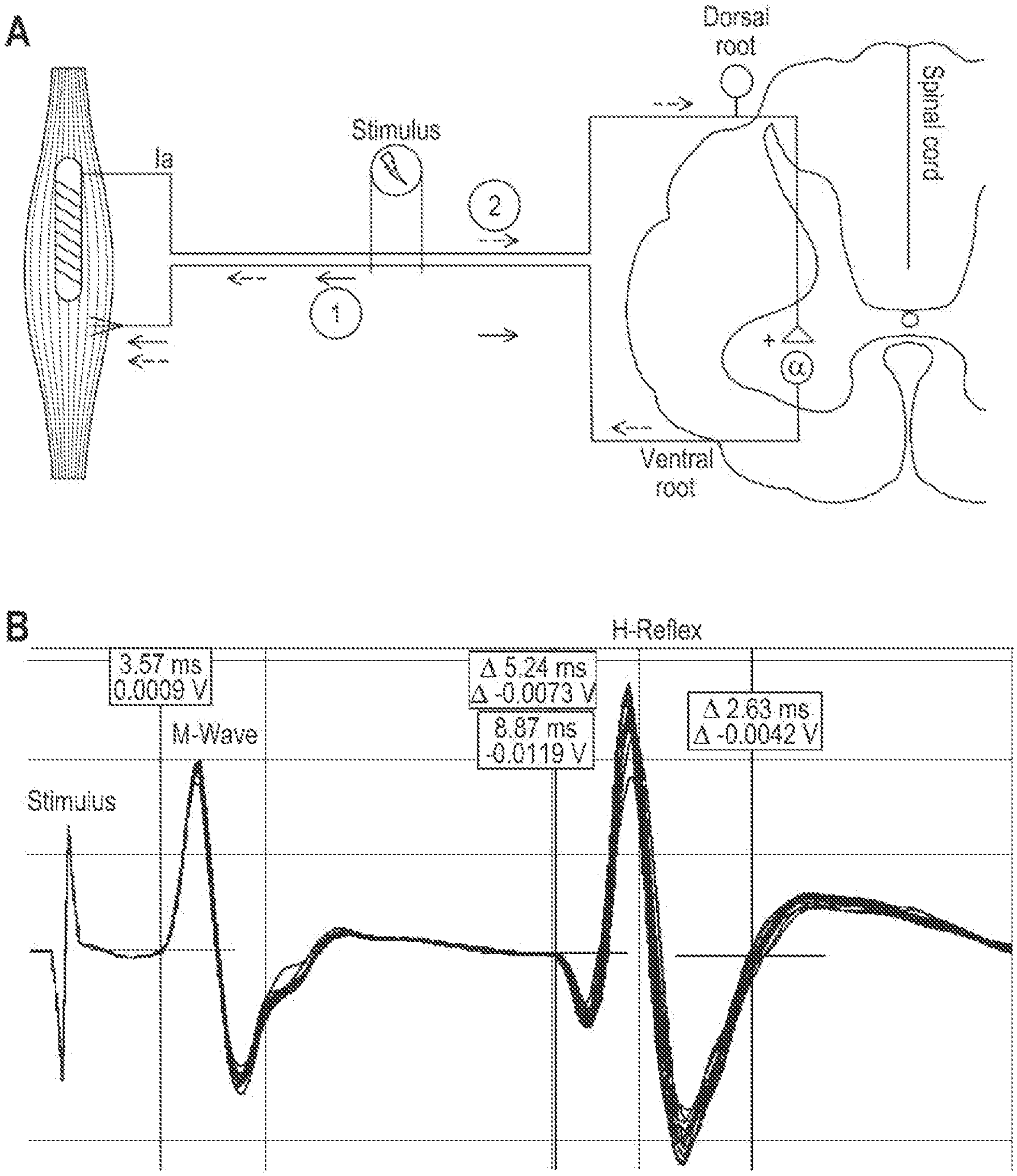
FIG. 6 represents the Hoffmann reflex, wherein (A) provides a schematic depicting the method of eliciting the Hoffmann reflex: 1) direct activation of motor axons, 2) monosynaptic activation of motoneuron (α) by 1a afferents; and (B) provides an example of electromyographic recording. Each trace is the response to one stimulation at 0.2 Hz.

Modulation of the RDD of the H-reflex. The Hoffmann reflex was used to assess primary (type 1a) afferents-mediated motoneuronal excitability in rats suffering from spasticity. Electromyograms typically show two responses: an initial M wave (FIG. 6B) resulting from the direct activation of motor axons (FIG. 6A-1), and a delayed H wave (FIG. 6B) resulting from the monosynaptic activation of motoneurons by the afferents (FIG. 6A-2).

Rate-dependent depression (RDD), a measure of the change in amplitude of the H-reflex over consecutive stimulations, is attenuated in SCI rats. To evaluate whether spastic symptoms, such as weakened RDD, were inhibited following single P.O. administration of Compound 1 (3, 10, 30 mg/kg), Baclofen (4.5 mg/kg), or Tizanidine (3 mg/kg), the amplitude of the H-reflex was measured before and 1, 2, 3, 4, 5, and 6 hours after administration. The mean relative amplitudes of the H-reflex were significantly reduced ($P<0.05$, $P<0.01$, $P<0.001$, $P<0.0001$; Kruskal-Wallis, Dunn's post-tests) in SCI rats administered with Compound 1 at 10 and 30 mg/kg doses, in SCI rats administered with Baclofen at 4.5 mg/kg, and in SCI rats administered with Tizanidine at 3 mg/kg.

To determine the level of RDD at different frequencies, the responses to the first three stimulations necessary for the depression to occur were discarded, and all the responses were expressed as percentages (%) relative to the mean response at 0.2 Hz in the same series of measurements. The H wave amplitude is attenuated by repeated activations at frequencies higher than 0.2 Hz, with a maximum reduction at 5 Hz in intact rats. The RDD was progressively reduced in animals with SCI, and this effect is a reliable correlate of the development of the spasticity. In this study, the RDD was significantly reduced (P<0.0001; Unpaired t-test) 5 weeks after complete transection of the spinal cord in rats. Before P.O. administration of the compounds, no differences (P>0.05; Unpaired t-test) were observed in the mean relative amplitudes of the H-Reflex between the seven test groups for each frequency.

Figure 7:
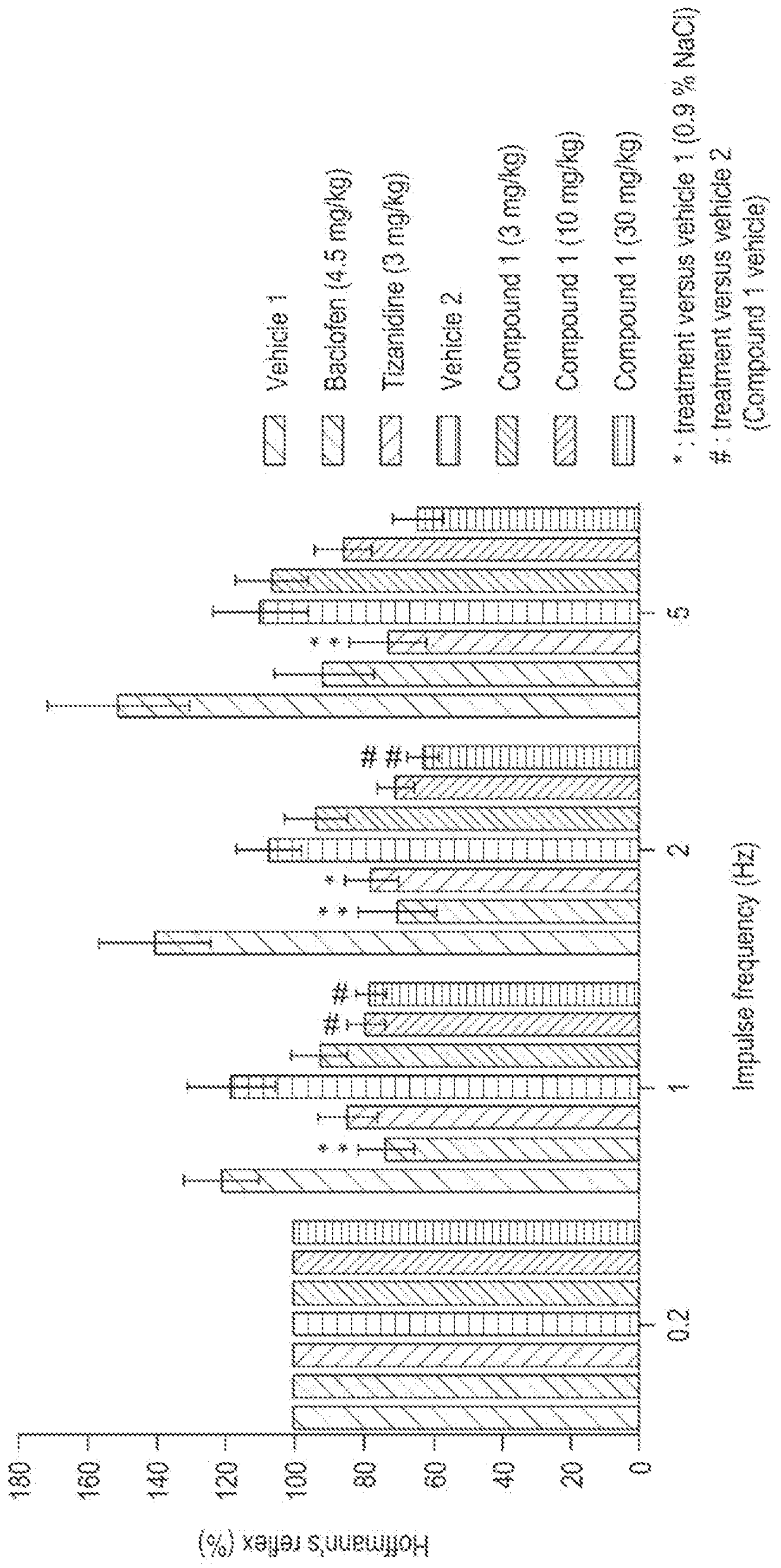
FIG. 7 shows that the effect of Compound 1 (10, 30 mg/kg) on the mean relative amplitudes of the H-reflex persisted for at least 6 hours.

As shown in FIG. 7, a single P.O. dose of 10 mg/kg of Compound 1 exhibited an onset of action of 1 h (P<0.05 at 1 Hz) and a duration of action of at least 6 hour (P<0.05 at 1 Hz). At 30 mg/kg, Compound 1 exhibited an onset of action of 1 hour (P<0.01 at 1 Hz, P<0.001 at 2 Hz. and P<0.05 at 5 Hz) and a duration of action of at least 6 hours (P<0.05 at 1 Hz, P<0.01 at 2 Hz). Compound 1 did not appear to affect spasticity when administered at a dose of 3 mg/kg.

By comparison, Baclofen (4.5 mg/kg) exhibited an onset of action of 1 hour (P<0.05 at 1 Hz, P<0.01 at 2 Hz, P<0.05 at 5 Hz), a maximum effect of 5 hours (P<0.001 at 1 Hz, P<0.0001 at 2 Hz, P<0.01 at 5 Hz) and a duration of action of at least 6 hours (P<0.01 at 1 Hz, P<0.01 at 2 Hz). Tizanidine (3 mg/kg) exhibited an onset of action and a maximum effect of 2 hours (P<0.01 at 1 Hz, P<0.001 at 2 Hz, P<0.05 at 5 Hz), and a duration of action of at least 6 hours (P<0.05 at 2 Hz, P<0.01 at 5 Hz).

Figure 8:
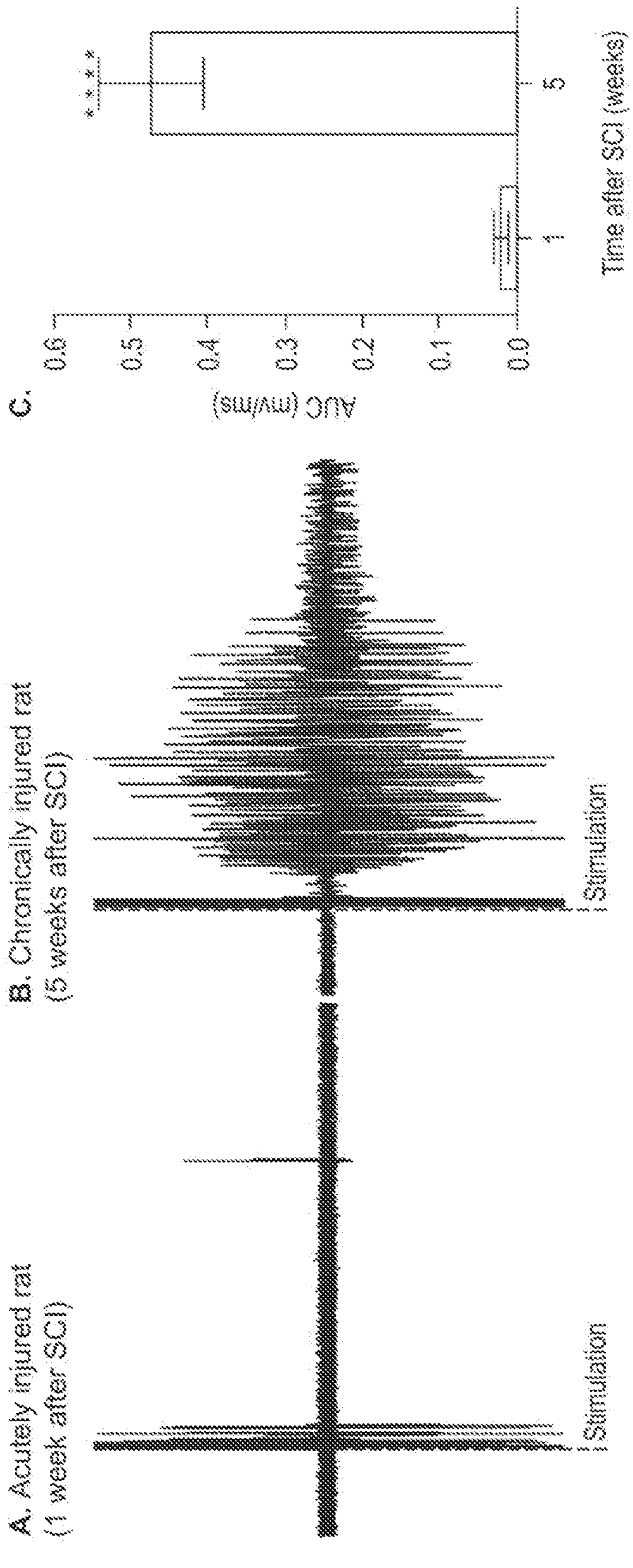
FIG. 8 shows how more spastic long-lasting muscle contractions are produced in chronic SCI rats, wherein: (A) shows FDB EMG responses to stimulation of the tibial nerve (single pulse every 60 sec, 10 sweeps) in acute SCI rat (1 week after injury); (B) shows the effect in chronic SCI rat (5 weeks after injury); and (C) shows how more spastic long-lasting muscle contractions are produced in chronic SCI rats (n=70) than acute SCI rats (n=8; ****P<0.0001; Mann-Whitney test). Data are expressed as mean±SEM.

Modulation of Muscle Spasms. When the tibial nerve was stimulated in acutely (1 week after injury) injured rats, little reflexes were evoked in the FDB muscle (FIG. 8A), regardless of the stimulation intensity. In contrast, stimulation of the tibial nerve in chronic (5 weeks after injury) SCI rats produced more (P<0.0001; Mann-Whitney test; FIG. 8C) long-lasting muscle contractions (FIG. 8B). This effect is a reliable correlate of the development of spasticity. In spastic rats, spasms were induced through the FDB muscle after electrical stimulation of the tibial nerve. Responses were typically characterized by a sustained muscle contraction that lasted for several seconds (FIG. 8B).

Figure 9:
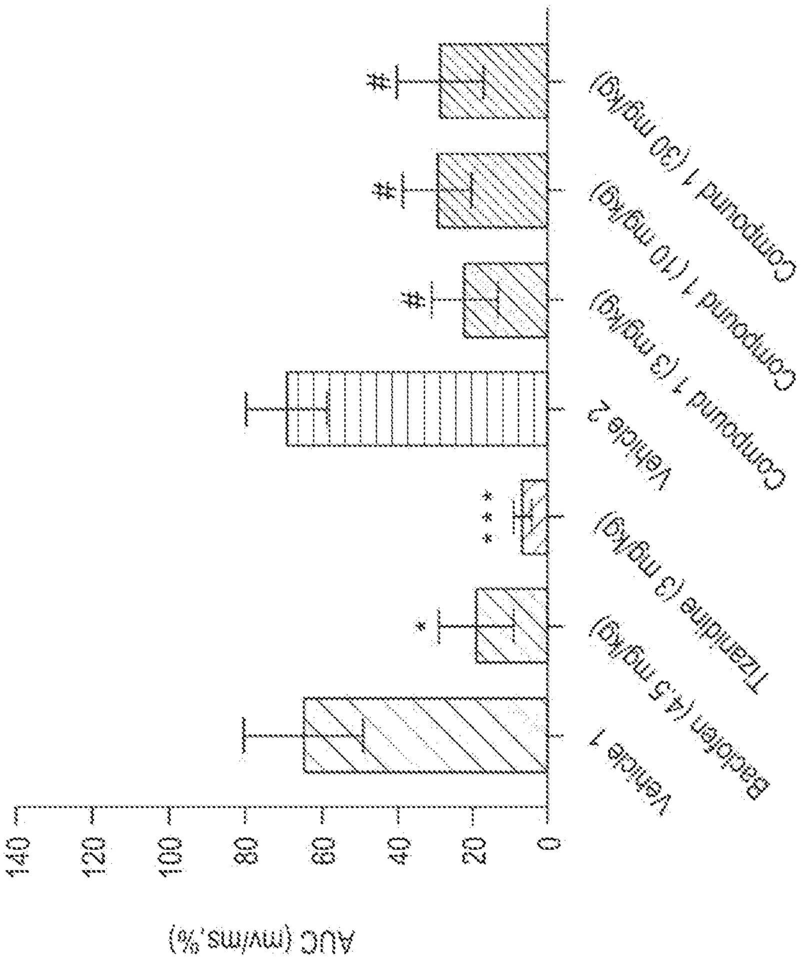
FIG. 9 shows the dose-dependent reduction of muscle spasms in SCI rats 3 hours post-dose.

Muscle spasms (AUC) were significantly reduced (P<0.05, P<0.01, P<0.001; Kruskal-Wallis, Dunn's post-tests) in SCI rats (n=10) administered with Compound 1 at all tested dosages. Muscle spasms were also reduced in SCI rats administered with Baclofen (4.5 mg/kg) and Tizanidine (3 mg/kg). This effect was specific to the long-lasting tonic activity as none of the parameters characterizing M and H waves were changed (p>0.05; Kruskal-Wallis, Dunn's post-test). FIG. 9 shows the compounds' effect three hours post-dose.

After single P.O. administration, Compound 1 (3, 10, 30 mg/kg) exhibited an onset of action of 1 hour (P<0.05, P<0.01), 1 hour (P<0.01), 1 hour (P<0.01), and 4 hours (P<0.01) respectively, and a duration of action of 5 hours (P<0.05), 3 hours (P<0.05), and 5 hours (P<0.05) respectively. By comparison, Baclofen (4.5 mg/kg) exhibited an onset of action of 1 hour (P<0.05), a maximum effect of 2 hours (P<0.01), and a duration of action of at least 6 hours (P<0.01). Tizanidine (3 mg/kg) exhibited an onset of action of 2 hours (P<0.01), a maximum effect of 3 h (P<0.001), and a duration of action of at least 6 hours (P<0.01).

In conclusion, complete thoracic spinal cord transection in adult rats induces spasticity, as evidenced by the weakened H-reflex RDDs and the emergence of muscle spasms. The relevance of the model is confirmed by the efficacy obtained with Baclofen (4.5 mg/kg; GABA B receptor activator) and Tizanidine (3 mg/kg; central alpha-2-adrenergic receptor agonist), both of which are currently used in patients. In this rat model of spasticity, orally administered Compound 1 demonstrated an antispastic therapeutic effect at 10 and 30 mg/kg doses. This efficacy was demonstrated on the two parameters that define spasticity: hyperexcitability of the stretch reflex and spasms. Among the compounds evaluated in this model, Compound 1 is the first to demonstrate therapeutic efficacy by oral administration.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Each of the references disclosed herein is incorporated herein in its entirety.

What is claimed is:

1. A method of treating or preventing cerebral spasticity, which comprises administering a therapeutically or prophylactically effective amount of an adaptor associated kinase 1 (AAK1) inhibitor to a patient in need thereof, wherein the AAK1 inhibitor is a compound of Formula (I):

(I)

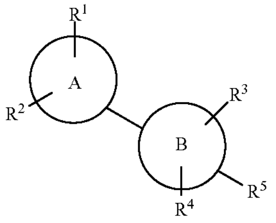

or a pharmaceutically acceptable salt thereof, wherein:

A is selected from

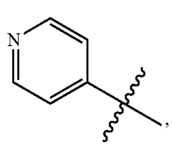,

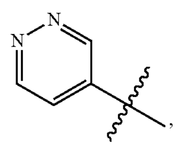,

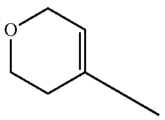

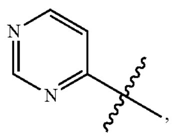,

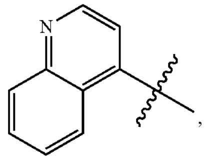,

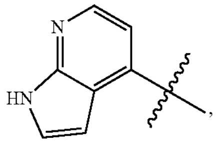,

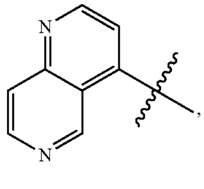, and

-continued

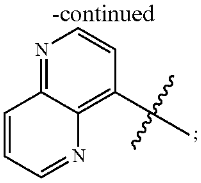;

wherein " " denotes the point of attachment to B;

B is selected from

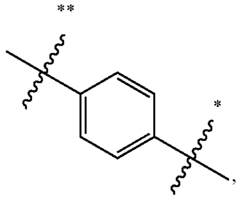,
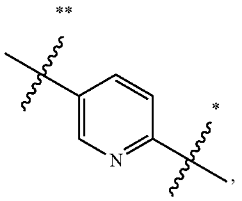,
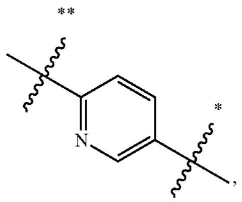,
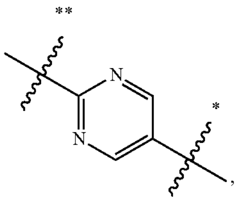,
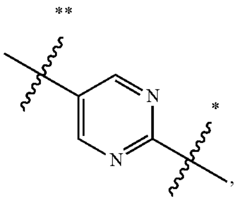, and
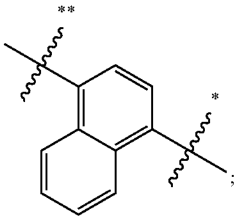;

wherein "*" indicates the point of attachment to $R^5$ and "**" indicates the point of attachment to ring A;

$R^1$ is selected from hydrogen, amino, —$CO_2H$, difluoromethyl, ethyl, halo, hydroxymethyl, methoxy, methyl, —$NHC(O)CH_3$, —$NHCO_2CH_3$, trifluoromethoxy, and trifluoromethyl;

$R^2$ is selected from hydrogen, cyano, —$CH_2OH$, halo, and methyl;

$R^3$ is selected from hydrogen, cyano, cyclopropyl, difluoromethyl, halo, hydroxymethyl, methoxy, methyl, methylsulfonyl, trifluoromethoxy, trifluoromethyl, —$CH_2N(CH_3)_2$, and a five-membered aromatic ring containing one, two, or three heteroatoms selected from nitrogen, oxygen, and sulfur;

$R^4$ is selected from hydrogen, halo, and methyl;

$R^5$ is selected from

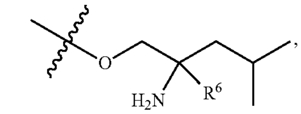,
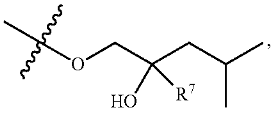, and

-continued

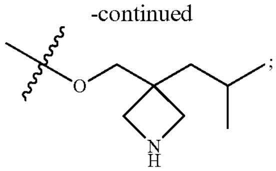;

$R^6$ is selected from hydrogen, ethyl, fluoromethyl, difluoromethyl, methyl, and trifluoromethyl; and $R^7$ is methyl.

2. The method of claim 1, wherein the AAK1 inhibitor is a compound of Formula (II):

(II)

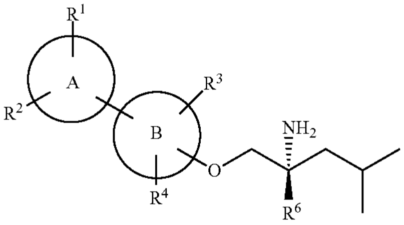

or a pharmaceutically acceptable salt thereof, wherein:

A is selected from

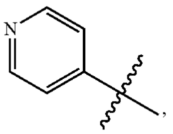,
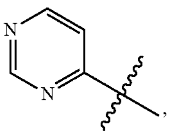,
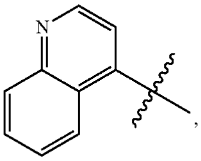,
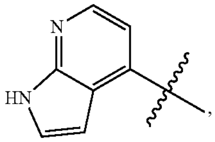,
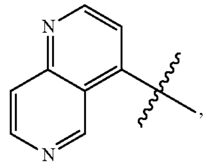, and
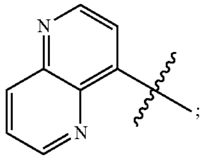;

$R^1$ is selected from hydrogen, difluoromethyl, halo, methoxy, methyl, —$NHC(O)CH_3$, —$NHCO_2CH_3$, and trifluoromethyl;

$R^2$ is selected from hydrogen, —$CH_2OH$, and halo; and $R^3$ is selected from hydrogen, cyano, cyclopropyl, difluoromethyl, halo, hydroxymethyl, methoxy, methyl, trifluoromethoxy, trifluoromethyl, and a five-membered aromatic ring containing one, two, or three heteroatoms selected from nitrogen, oxygen, and sulfur.

3. The method of claim 2, wherein A is

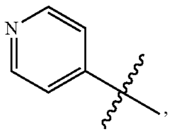,
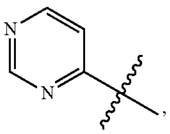, or

-continued

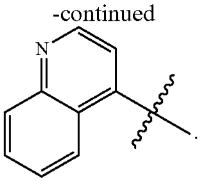

4. The method of claim 2, wherein B is

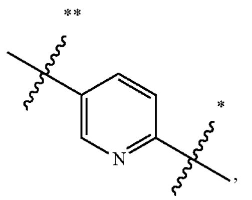

or

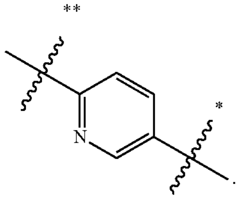

5. The method of claim 1, wherein the patient suffers from amyotrophic lateral sclerosis, cerebral palsy, multiple sclerosis, or stroke.

6. A method of treating or preventing cerebral spasticity which comprises administering a therapeutically or prophylactically effective amount of an adaptor associated kinase 1 (AAK1) inhibitor to a patient in need thereof, wherein the AAK1 inhibitor is(S)-1-((2',6-bis(difluoromethyl)-[2,4'-bipyridin]-5-yl)oxy)-2,4-dimethylpentan-2-amine:

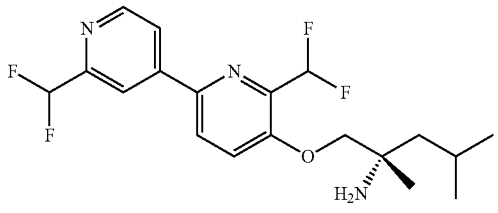 [SMILES: CC(C)C[C@](C)(N)COc1ccc(-c2ccnc(C(F)F)c2)nc1C(F)F]

or a pharmaceutically acceptable salt thereof.

7. The method of claim 6, wherein the AAK1 inhibitor is ((S)-1-((2',6-bis(difluoromethyl)-[2,4'-bipyridin]-5-yl)oxy)-2,4-dimethylpentan-2-aminium dihydrogen phosphate.

8. The method of claim 7, wherein the AAK1 inhibitor has a melting point of 184±2° C.

9. The method of claim 6, wherein the patient suffers from amyotrophic lateral sclerosis, cerebral palsy, multiple sclerosis, or stroke.

10. The method of claim 6, wherein the AAK1 inhibitor is administered orally.

* * * * *